US006673008B1

(12) United States Patent
Thompson et al.

(10) Patent No.: US 6,673,008 B1
(45) Date of Patent: Jan. 6, 2004

(54) FALLOPIAN TUBE AND METHOD OF IN VITRO FERTILIZATION AND EMBRYO DEVELOPMENT

(76) Inventors: Ronald J. Thompson, 110 Stanbery Ridge, Ft. Thomas, KY (US) 41075; Michael J. Campbell, 1606 Greenbrook Pl., Louisville, KY (US) 40245

( * ) Notice: Subject to any disclaimer, the term of this patent is extended or adjusted under 35 U.S.C. 154(b) by 0 days.

(21) Appl. No.: 09/450,963

(22) Filed: Nov. 30, 1999

Related U.S. Application Data

(63) Continuation-in-part of application No. 09/067,715, filed on Apr. 28, 1998, now abandoned.

(51) Int. Cl.[7] .............................................. A61B 17/43
(52) U.S. Cl. ........................... 600/33; 600/34; 600/35; 435/290.4
(58) Field of Search ............................. 600/33, 34, 35; 435/290.4; 128/898

(56) References Cited

U.S. PATENT DOCUMENTS

| 2,723,660 A | 11/1955 | Greenberg |
| 3,121,961 A | 2/1964 | Engle et al. |
| 4,033,825 A | 7/1977 | Haddad et al. |
| 4,137,922 A | 2/1979 | Leininger et al. |
| 4,159,009 A | 6/1979 | Friedman |
| 4,160,446 A | 7/1979 | Barrington |
| 4,182,328 A | 1/1980 | Bolduc et al. |
| 4,201,845 A | 5/1980 | Feder et al. |
| 4,547,188 A | 10/1985 | Bolduc |
| 4,563,172 A | 1/1986 | Ferguson |
| 4,574,000 A | 3/1986 | Hunter |
| 4,654,025 A | 3/1987 | Cassou et al. |
| 4,701,161 A | 10/1987 | Lenck |
| 4,734,372 A | 3/1988 | Rotman |
| 4,781,706 A | 11/1988 | Suzuki et al. |
| 4,809,860 A | 3/1989 | Allen |
| 4,839,292 A | 6/1989 | Cremonese |
| 5,079,160 A | 1/1992 | Lacy et al. |
| 5,104,377 A | 4/1992 | Levine |

(List continued on next page.)

FOREIGN PATENT DOCUMENTS

| GB | 1539263 | 1/1979 |
| WO | WO8203227 | 9/1982 |
| WO | WO8706257 | 10/1987 |
| WO | WO9006990 | 6/1990 |
| WO | WO9207063 | 4/1992 |

OTHER PUBLICATIONS

Australian Journal of Soil Research, vol. 35 (1997), 9 pgs., CSIRO Publishing.
*Stem Cell Technologies Fight for the Limelight*, NEWS, p. 572, Issue 9, vol. 88, jnci, (1996) 4 pgs.
In Vitro Cell. Dev. Biol. 30A–819–821, Dec. 1994, ©1994 Society for In Vitro Biology, Letter to the Editor—*The Development of a Superfusion System for Studying Intracellular and Secretory Processes in Embryos.*
J. Reprod. Fert., Suppl. 44 (1991), 405–410, ©1991 Journals of Reproduction & Fertility Ltd.—*Viability and ultrastructure of equine embryos following culture in a static or dinamic system*—J. A. Pruitt, et al.
Theriogenology 46: 1441–1450, 1996, © 1996 by Elsevier Science Inc., *A Continuous Flow, Perifusion Culture System for 8– to 16–Cell Bovine Embryos Derived From In Vitro Culture*, J. M. Lim, et al.

*Primary Examiner*—Rosiland S. Kearney
(74) *Attorney, Agent, or Firm*—John E Vanderburgh; Stites & Harbison

(57) ABSTRACT

A device for the in vitro development of an embryo in a fluid. A method for the in vitro development of an embryo in a fluid is also provided.

26 Claims, 15 Drawing Sheets

U.S. PATENT DOCUMENTS

| | | |
|---|---|---|
| 5,108,366 A | 4/1992 | Schatz |
| 5,218,958 A | 6/1993 | Cooper |
| 5,223,151 A | 6/1993 | Rojas |
| 5,261,255 A | 11/1993 | Coelho et al. |
| 5,326,706 A | 7/1994 | Yland et al. |
| 5,372,584 A | 12/1994 | Zink et al. |
| 5,374,247 A | 12/1994 | Lowery et al. |
| 5,385,821 A | 1/1995 | O'Dell et al. |
| 5,416,022 A | 5/1995 | Amiot |
| 5,459,069 A | 10/1995 | Palsson et al. |
| 5,466,603 A | 11/1995 | Meehan et al. |
| 5,472,876 A | 12/1995 | Fahy |
| 5,484,731 A | 1/1996 | Stevens |
| 5,505,716 A | 4/1996 | Simmet et al. |
| 5,512,476 A | 4/1996 | Gordon |
| 5,514,119 A | 5/1996 | Curtis |
| 5,558,636 A | 9/1996 | Li et al. |
| 5,562,654 A | 10/1996 | Smith |
| 5,565,353 A | 10/1996 | Klebe et al. |
| 5,605,822 A | 2/1997 | Emerson et al. |
| 5,624,399 A | 4/1997 | Ackerman |
| 5,646,043 A | 7/1997 | Emerson et al. |
| 5,656,010 A | 8/1997 | Li et al. |
| 5,665,599 A | 9/1997 | Minuth |
| 5,681,742 A | 10/1997 | MersKelly et al. |
| 5,688,687 A | 11/1997 | Palsson et al. |
| 5,763,266 A | 6/1998 | Palsson et al. |
| 5,780,294 A | 7/1998 | Stevens et al. |
| 5,824,548 A * | 10/1998 | Hearn ................ 435/325 |
| 5,827,174 A | 10/1998 | Reuss, Jr. et al. |
| 5,985,653 A | 11/1999 | Armstrong et al. |

* cited by examiner

FALLOPIAN TUBE AND METHOD OF IN VITRO FERTILIZATION AND EMBRYO DEVELOPMENT

This application is a continuation-in-part of application Ser. No. 09/067,715, which was filed on Apr. 28, 1998, now abandoned.

TECHNICAL FIELD OF THE INVENTION

The present invention relates to apparatus and methods for the development of an embryo outside the body, and more specifically, to apparatus and methods of providing the optimal environment for embryo development until the embryo is ready for implantation into the body.

BACKGROUND OF THE INVENTION

About every 28 days or so, the post-pubescent female human goes through the reproductive cycle. The cycle is divided into two phases: the follicular phase (generally the first 14 days, or half of the cycle); and the luteal phase (generally the last 14 days, or half of the cycle).

During the follicular phase, the anterior pituitary gland secretes follicle stimulating hormone (FSH), which is a small glycoprotein. The ovaries have a specific receptor cite for the FSH. FSH assists in the development of one or two small cysts (i.e., egg follicles) in the ovaries, each of which contains an ovum. Cells surrounding the developing ovum, in turn, produce estrogen. Estrogen has several effects on the body during the follicular phase. First, it stimulates development of the endometrium: the velvet-like interior lining of the uterus which allows the uterus to receive and support an embryo. Secondly, estrogen regulates the release of FSH from the anterior pituitary gland. At low levels, estrogen modulates the release of FSH. However, at higher levels, estrogen provides a positive feedback on the pituitary gland, inhibiting the release of FSH and stimulating the release of luteinizing hormone ("LH").

LH is released from the anterior pituitary gland on about day 13 of the reproductive cycle. LH assists in causing ovulation: the release of an ovum (i.e., egg) from its follicle. Distal fingers or frimbrae of a fallopian tube embrace or pick up the ovum and envelope it in the distal portion of the fallopian tube, also known as the ampullae.

The ampullae is an about 2 to about 2.5 cm tubal segment of the fallopian tube having a diameter of about 1 to about 2 cm. Fertilization (union of the capacitated sperm and ovum) occurs in this portion of the fallopian tube. After fertilization, the. fertilized ovum (or embryo) slowly migrates along the fallopian tube towards the uterus. The embryo spends its first 2 to 3 days in the ampullae where the embryo (commonly referred to as a zygote at this stage of development) rapidly divides into a ball of cells.

The interluminal environment of the fallopian tube consists of a serum transudate, which is produced from the epithelial cell lining of the fallopian tube's lumen. A rich vascular supply exists along the entire length of the fallopian tube, with collateral circulation from both the uterine and ovarian arteries and veins. The serum transudate establishes an equilibrium with the epithelial cell arterioles and capillaries to supply nutrients, glucose, amino acids, and oxygen to the developing embryo in the fallopian tube. Moreover, metabolic waste, including carbon dioxide, is evacuated from serum transudate by diffusion into the capillaries. The constant supply of nutrients, glucose, amino acids, and oxygen to the developing embryo and the rapid elimination of metabolic waste, including carbon dioxide, provides an optimum environment for embryo development in the fallopian tube.

There are generally two methods of transportation of the embryo through the fallopian tube. First, the fallopian tube contracts as a muscle to move the embryo along its length towards the uterus. Second, fallopian tube epithelial cell cilia assist in moving the ovum or embryo from the ovary to the uterus. In fact, the cilia (hair like projections) create a current in the serum transudate. Both the muscle contraction and the cilia movement create a "to-and-fro" or "back-and-forth" movement within the fallopian tube. This movement of the serum transudate (i.e., fluid in the fallopian tube) and embryo creates an intraluminal circulation system which assists in distributing nutrients and oxygen to the embryo, and removing metabolic waste (including urea and carbon dioxide) away from the embryo.

After ovulation, the reproductive cycle enters the luteal phase, wherein the ovaries secrete progesterone at the cite of ovulation. The cite of ovulation on the ovary is yellow and is commonly referred to as the corpus luteum. Progesterone stops the estrogen-mediated growth of the endometrium, and maintains the endometrium so as to prepare it for the reception and support of the developing embryo.

After fertilization, the embryo begins its migration toward the uterus. At first, the rate of travel is slow and the distance of travel is short. For example, about one day after fertilization, the embryo has traveled about 1 cm through the fallopian tube toward the uterus. The rate of travel and distance traveled increases as time after fertilization elapses, and as the number of cells increases. For example, the embryo may travel another cm between day 1 and 2 post fertilization, and between day 2 and 3 post fertilization. However, the rate and distance of travel increases whereby the embryo may travel 3 cm between day 4 and 5 post fertilization (See, e.g., FIGS. 4–5).

As the embryo migrates toward the uterus, it leaves the ampullae and enters the isthmus, the longest section of the fallopian tube at about 4 to 7 cm. The isthmus has both circular and longitudinal muscles which assist in the migration of the embryo toward the uterus. The embryo spends about 40–60 hours migrating through the distal portion of the isthmus, and about 15–20 hours migrating through the proximal portion of the isthmus. Thereafter, the embryo passes through the cornu and interstitial regions of the fallopian tube, taking about 3–4 hours to do so. As the embryo's cell number increases from about 2 at day one post fertilization to about 32 at five days post fertilization (see, e.g., FIG. 6), its transit rate through the fallopian tube also increases. The increased transit rate is believed to assist in providing or making available additional nourishment to the embryo, and also to increase the rate of diffusion of waste products away from the embryo.

At about five days post fertilization (i.e., about 19 days into the reproductive cycle), the embryo enters the uterus. At this stage, the embryo is generally referred to as a blastocyst. The blastocyst may penetrate the endometrium whereby it implants and attaches to the uterine wall. At the point of implantation, the blastocyst divides into two distinct cell lines: the placental line, which will eventually develop into the placenta which assists in nourishing the fetus; and the fetal line. The placental line produces human chorionic gonadotrophin (HCG), which acts to continue the ovarian corpus luteum's production of progesterone for about 11 to 12 weeks (until the placenta has sufficient progesterone to continue the pregnancy).

Many women cannot become pregnant for a variety of reasons. For example, occlusion or dysfunction of the fallopian tubes may lead to fertility problems. One of the traditional solutions to infertility has been adoption. However, the number of healthy infants available for adoption relative to the number of people seeking to adopt has substantially decreased in recent years. As such, adoption often is not readily available to every person who wishes to adopt a child.

Alternatively, there have been attempts in the past to restore normal tubal function to occluded or dysfunctioning fallopian tubes. Surgeons have tried to repair or reconstruct damaged fallopian tubes using surgery. In addition, physicians have also tried transplanting healthy fallopian tubes from a donor. There are several drawbacks with this course of treatment. First, major surgery can be required under a general anesthetic. Second, with regard to transplant, there is the possibility of open rejection by the recipient.

Another solution to a dysfunctional fallopian tube has been to implant an artificial fallopian tube in the woman's body. An example of this is disclosed in U.S. Pat. No. 4,574,000 (Hunter). The apparatus includes a ovisac which encapsulates one of the ovaries in order to collect any ova discharge. Fluid supply tubes wash the ova toward a tubular member that is secured in communication with the uterine cavity. A reservoir of fluid and a programmable micropump are also provided, and are adapted to be implanted into the patient. The artificial fallopian tube, however, has several drawbacks. First, a patient's natural fallopian tube must be excised and the artificial fallopian tube inserted in its place. Such a procedure requires major surgery with a general anesthetic to implant. In addition, fluid used to wash the ova toward the tubular member and the uterine cavity must be injected into the reservoir through the skin using a syringe and needle, as needed.

Another alternative for the dysfunctioning fallopian tube is to totally bypass damaged fallopian tubes and use an in vitro fertilization ("IVF") technology (which is often referred to as "test tube babies"). This delicate procedure involves surgically removing a mature egg (an ovum) immediately prior to ovulation and placing it in a nutrient medium containing sperm. The sperm then fertilizes the ovum. Every 24 hours, the media is changed, generally by skilled embryologists, technicians, or physicians who physically move the embryo to another petri dish with fresh IVF media.

When in vitro fertilization was developed about 20 years ago, the embryo was transferred back to the body about 24 hours after fertilization. Since that time, the timing of the embryo's transfer back into the body has increased from 1 day after fertilization to about 3 days after fertilization. There are, however, several drawbacks with this procedure and the equipment used.

At one to three days after fertilization, the embryo has not sufficiently matured so that it is ready for attachment and implantation to the endothelium of the uterus. One solution to this has been to insert the embryo into the portion of the fallopian tube where it would typically be located at three days after fertilization. This procedure is commonly referred to as Zygote, Intra Fallopian Transfer or ZIFT. Then, the fallopian tube should transport the embryo to the uterus and allow it to develop inside the body (in vivo) and the fallopian tube over the next several days. However, this procedure has certain drawbacks. For example, it has increased the risk of a tubal pregnancy, which is where the embryo implants in the fallopian tube. Such a pregnancy cannot continue and has to be terminated. If this condition or type of pregnancy is not detected, the growing embryo can damage and even rupture the fallopian tubes.

At day three of embryo development in an IVF procedure, the embryo often is too young to properly evaluate. More specifically, the embryo has not developed sufficiently or for a period of time whereby its progress can be tracked and charted to predict a successful pregnancy. As such, the embryo may not be sufficiently developed or had its progress charted so as to predict whether or not the embryo will result in a pregnancy, or whether the embryo has a lethal defect due to genetics or a toxin.

In order to improve the likelihood of a successful pregnancy, multiple embryos (as many as 4 or 5) may be inserted into the uterus at one time in the hope that one embryo will attach to the endometrium. However, in many cases, more than one embryo, and sometimes all of the embryos, attach to the endometrium, which creates a multiple embryo pregnancy. Multiple birth pregnancies have a higher risk for the mother and the embryos as compared to a single embryo pregnancy. Concerns and problems can include increased chances of premature delivery, lower birth weight babies, toxemia in the mother, and twin to twin transfusion. Even when multiple embryos are inserted, the success rate as measured by the percentage of implantations, and thus pregnancies, has been relatively low, at about 6–7% per ovum transferred.

Previously, the ovum was fertilized in a petrie dish and allowed to develop in another petrie dish. As the needs of the embryo changed, it was physically removed from a first petrie dish and placed in another petrie dish with new fluid. In addition, in order to inspect the embryo to monitor and record its development, the embryo would have to be manipulated with a pipette. As the embryo remained in the petrie dish, the media was generally stagnant and did not move or even swirl around the embryo.

This procedure has several drawbacks. First, it can be costly since it involves the use of special laboratories and skilled technicians to maintain the developing embryo. Second, fluid within the petrie dish remains stagnant and a circulation system for distribution of nutrients and removal of waste products is not present. Moreover, the low success rate, as measured in successful pregnancies, may necessitate multiple attempts at embryo implantation. These additional attempts can further increase the cost.

Recently, there has been a teaching that an embryo can be maintained in vitro for four to five days after fertilization (i.e., until the embryo reaches the blastocyst stage) and then inserted into the uterus for implantation. Dr. D. K. Gardner reported the use of a serum-free media, and the use of a different liquid media for the period exceeding 2–3 days after fertilization. The teachings and techniques of Dr. Gardner, however, do not address the concerns of circulating media around the embryo while in vitro, and/or eliminating manipulation of the embryo while in vitro.

As can be seen, currently available equipment and techniques have a number of shortcomings that can greatly reduce the ability of the embryo to develop in vitro and thus, the success rate for in vitro pregnancies. The current structures and assemblies provide a petrie dish and other equipment that require physical manipulation of the embryo, and moving it from one petrie dish to another to change the media solution. A need currently exists in the fertility medicine field for equipment and techniques to enhance development of an embryo in vitro before being implanted in the body, which increases the chances or opportunity for pregnancy to occur when in vitro fertilization is used. As such, the chances for pregnancy increase when in vitro fertilization is used.

SUMMARY OF THE INVENTION

It is an object of the present invention to provide apparatus and techniques which address and overcome the above-mentioned problems and shortcomings in the fertility medicine field.

Another object of the present invention is to provide apparatus and techniques which mimic the physiology of the internal fallopian tube.

Still another object of the present invention is to provide apparatus and methods which allow for the replacement of the IVF media without the need to manipulate the embryo.

Yet another object of the present invention is to provide apparatus and methods which change the embryo growth conditions as the metabolic needs of a developing embryo change.

A further object of the present invention is to provide apparatus and methods which permit visualization of the developing embryo, without physically manipulating the embryo.

Yet another object of the present invention is to provide apparatus and methods which permit photo documentation of the developing embryo.

Another object of the present invention is to provide apparatus and methods which allow for the sequential monitoring of the embryo.

Still another object of the present invention is to provide apparatus and methods which allow development of multiple embryos in vitro, and selection of one or more of the embryos for implantation into the female.

A further object of the present invention is to provide apparatus and methods that can be used with genetic engineering or animal husbandry.

It is yet another object of the present invention is to provide apparatus and methods that permit the growth and development of the embryo to be monitored and charted.

Additional objects, advantages and other features of the invention will be set forth and will become apparent to those skilled in the art upon examination of the following, or may be learned with practice of the invention. It should also be understood that the objects specifically identified above may or may not be provided by each and every embodiment of the present invention. Thus, these objects of the present invention are not to be construed as limiting in any way the scope of the claims appended hereto.

One embodiment of the present invention comprises a device for the in vitro development of an embryo in a fluid that includes a chamber having a tank receiving the fluid. The chamber has an container for housing the embryo and a circulator therein for the circulation of fluid, or exterior for movement of the chamber and fluid therein. At least one fluid reservoir is in fluid communication with the chamber and a collector reservoir can also be in fluid communication with the chamber. In a preferred embodiment of the present invention, the chamber may include at least one inlet port provided in the lower portion of the chamber, and/or an outlet port provided in the upper portion of the chamber.

The container can include at least one window whereby a visualization assembly can monitoring the inside of the container through the window or within the chamber. In a preferred embodiment, two windows may be oppositely disposed in the sides of the container. To permit or enhance the circulation of fluid around the embryo, the container may be made from a microporous material, preferably having a pore size of less than about 75 microns.

The present invention may also include a visualization assembly to monitor, visualize, and/or record the development and progress of the embryo, and/or the ovum and sperm before fertilization. The visualization assembly can include a viewing device, such as a magnification device to enhance the view of the contents, and/or a photodocumentation device, such as a camera. Additionally, the visualization assembly may also include a display device that can preferably be located away or remote from the chamber, or a printer.

The present invention can also include a sensor system in the chamber for monitoring the condition of the fluid. The sensor system can include different types of sensor, such as a pH sensor, an oxygen sensor, a thermometer, or a carbon dioxide sensor.

The present invention may also include a feedback control system that can have a microprocessor; and a sensor system in electrical communication with the microprocessor, a pump in electrical communication with the microprocessor, a valve in electrical communication with the microprocessor, a temperature regulator in electrical communication with the microprocessor, or a circulator in electrical communication with the microprocessor.

The present invention also includes a method for the in vitro development of an embryo in a fluid, preferably until it reaches the blastocyst stage. An embryo or sperm and an ovum can be placed in container that is placed in a chamber for holding the fluid. Fluid within the chamber is circulated. Fluid is then selectively exchanged in the chamber. Exchanging the media can include removing fluid from the chamber to the collection reservoir, and inserting fluid from the reservoir into the chamber. This can occur simultaneously. Conditions of the fluid, such as pH levels, temperature, oxygen levels, or carbon dioxide levels can be monitored and displayed by a sensor system in the fluid.

Fluid in the chamber can be exchanged at predetermined time interval, of if the conditions in the fluid warrant a change. Examples of such condition changes may include temperature, oxygen, or carbon dioxide levels above or below prescribed levels.

Development and progress of the ovum, sperm and embryo can be monitored, viewed and recorded using a visualization assembly.

After the embryo has sufficiently developed, preferably to the blastocyst stage, it is transferred from the device to uterus of a female.

The present invention also provides a method for the in vitro development of an embryo, comprising:

(a) providing a tank having an embryo and a first fluid therein;

(b) monitoring the growth of the embryo; and (c) adjusting conditions within the tank in response to the results of the monitoring step.

The step of monitoring the growth of the embryo may comprise, for example, monitoring the nuclear mass (i.e., cell count) of the embryo, such as by measuring the optical density of the embryo. The optical density of the embryo may be measured by directing light at the embryo, and measuring the amount of light transmitted through the embryo.

The step of adjusting conditions within the tank may comprise at least one of: adjusting the fluid pressure within the tank, flowing fluid into the tank and adjusting the temperature within the tank. By way of example, the fluid pressure within the tank may be increased as the nuclear mass of the embryo increases, thereby better simulating the conditions within a natural fallopian tube during transit of the embryo towards the uterus. The tank may include a fluid outlet, and the step of adjusting conditions within the tank may comprise adding new fluid to the tank while allowing the first fluid already in the tank to be removed from the tank through the fluid outlet. The new fluid may be the same as or different from the first fluid already in the tank. The step of adjusting conditions within the tank may also comprise replacing the first fluid with a second fluid after the nuclear mass of the embryo has reached a predetermined level, wherein the replacing step is accomplished without manipulating the embryo.

A plurality of tanks, each having an embryo and a first fluid therein, may also be provided. The step of monitoring the growth of the embryos may comprise monitoring the rate of growth of each embryo over a period of time, such that one or more of the embryos may be selected for insertion into a recipient based upon the rate of growth of those embryos (e.g., those embryos which grew at the optimal rate are chosen for implantation).

The present invention also provides a method for the in vitro development of an embryo, comprising:
  (a) providing a tank having an embryo therein, the tank in fluid communication with at least first and second sources of fluid;
  (b) flowing fluid from at least the first fluid source into the tank; and
  (c) thereafter, flowing fluid from at least the second fluid source into the tank.

The tank may have a fluid inlet and a fluid outlet, such that fluid is urged out of the tank through the fluid outlet as fluid is flowed into the tank through the fluid inlet. Fluid may be continuously flowed into the tank (e.g., gravity fed, gas pressure fed or pumped), or may be periodically flowed into the tank (e.g., pulsed flow, or even flowed into the tank at predetermined intervals dependant upon a predetermined schedule, embryo growth, a sensed condition within the tank, and/or a sensed condition of fluid urged out of the tank). In addition, the step of flowing fluid from at least the second fluid source into the tank may similarly commence in response to at least one of: a predetermined schedule, the nuclear mass of the embryo, a sensed condition within the tank, and a sensed condition of fluid urged out of the tank.

The present invention further provides a method of fertilizing an egg and for the in vitro development of the resulting embryo, comprising:
  (a) providing a tank having a fluid outlet and a fluid inlet;
  (b) inserting an unfertilized egg, a fluid, and sperm into the tank;
  (c) after the egg has been fertilized or after a predetermined period of time sufficient to allow the egg to be fertilized, flowing additional fluid into the tank through the fluid inlet, such that sperm and fluid already in the tank is urged out of the tank through the fluid outlet; and
  (d) allowing the fertilized egg to develop in the tank.

A cartridge for use in the in vitro development of one or more embryos is also provided by the present invention, and comprises:
  (a) a cartridge body; and
  (b) at least one tank for housing an embryo therein, the tank having a fluid inlet and a fluid outlet;
wherein the cartridge is configured such that it may be placed in fluid communication with at least one fluid source such that fluid from the fluid source may be delivered to the tank through the fluid inlet, and the cartridge is further configured such that fluid may be removed from the tank through the fluid outlet. The cartridge may even comprise a plurality of the tanks, each of the tanks having a fluid inlet and a fluid outlet. The cartridge body may include one or more cartridge fluid inlets, each of which is in fluid communication with the fluid inlet on the tank.

The tank may include an upper portion and a lower portion, wherein the diameter of the upper portion is greater than the diameter of the lower portion. The fluid outlet may be located on the lower portion of the tank, and the fluid inlet located on the upper portion of the tank. The lower portion of the tank may also include a porous wall adjacent the fluid outlet, the porous wall configured to allow fluid (and even sperm and cellular debris) to pass therethrough, while preventing an embryo from passing therethrough. The tank may also have a port configured for inserting an embryo therethrough, as well as a valve in fluid communication with the fluid outlet. The cartridge body may include a cartridge fluid outlet in fluid communication with the fluid outlet on the tank.

The present invention also provides a system for the in vitro development of one or more embryos, comprising:
  (a) a main housing for incubating at least one embryo therein, the housing configured for receiving a cartridge therein;
  (b) a cartridge positioned in the main housing, the cartridge having at least one tank configured for housing an embryo therein; and
  (c) one or more fluid sources for containing a fluid therein, at least one of the fluid sources in fluid communication with the at least one tank.

It should be pointed out that the phrase "fluid communication" includes the situation wherein a valve or other flow control member is interposed between the two items which are in fluid communication in order to control (and even prevent) the flow of fluid therebetween. The cartridge may have a plurality of tanks, each of which is configured for housing an embryo therein, and wherein the at least one fluid source is in fluid communication with the tanks.

The system mat further comprise at least one pump for urging fluid from the at least one fluid source into the at least one tank, as well as at least one valve for regulating the flow of fluid from the at least one fluid source into the at least one tank. A processor (e.g., a CPU of the type used in general purpose or specialized computing devices) for controlling the flow of fluid from the at least one fluid source into the at least one tank may also be provided. The system may also include a visualization system for acquiring an image of an embryo positioned within the tank, as well as a display screen configured for displaying an image acquired by the visualization system. The visualization system may comprise, for example, a camera configured for acquiring an image of an embryo positioned within the tank. In one embodiment, images of an embryo positioned within the tank may be acquired at predetermined intervals, and even automatically as controlled by the processor. The visualization system may further comprise one or more fiber optic bundles positioned within the cartridge, the fiber optic bundle configured for transmitting an image of an embryo positioned within the tank to the camera.

A control system for regulating fluid conditions within the tank may also be included, and may comprise a processor, at least one sensor in electrical communication with the sensor, and at least one processor-controlled device chosen from the group consisting of: a heater, a pump configured for urging fluid from the at least one fluid source into the at least one tank, and at least one valve for regulating the flow of fluid from the at least one fluid source into the at least one tank. The control system may further include at least one alarm responsive to an electrical signal from the processor.

The system may also include a waste fluid reservoir in fluid communication with the at least one tank, as well as a plurality of the cartridges.

BRIEF DESCRIPTION OF THE DRAWINGS

While the specification concludes with claims particularly pointing out and distinctly claiming the present invention, it is believed the same will be better understood from the following description, taken in conjunction with the accompanying drawings in which.

FIG. 15 is a perspective view of an exemplary IVFT device according to one embodiment of the present invention.

DETAILED DESCRIPTION OF THE PREFERRED EMBODIMENTS

Figure 1:
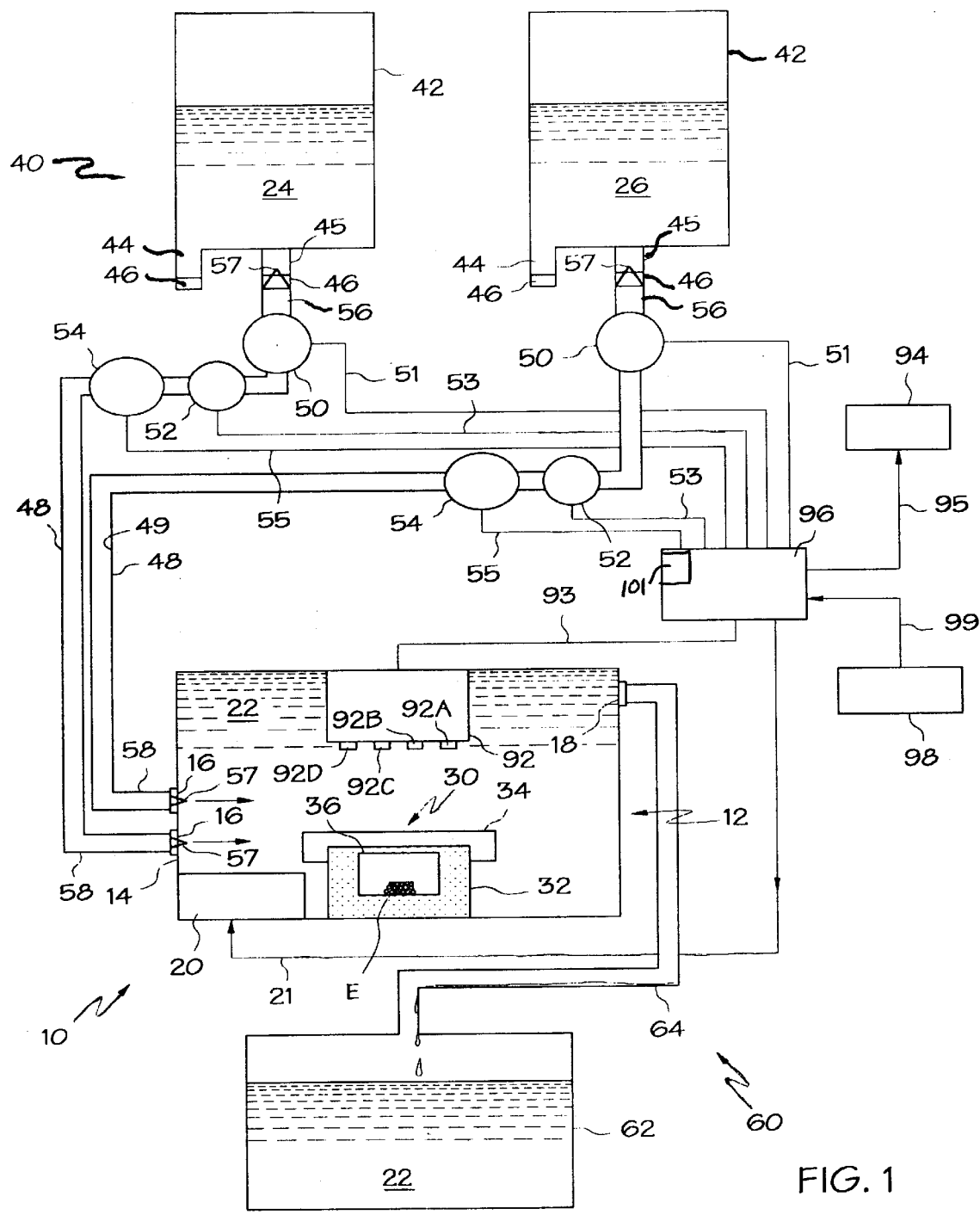
FIG. 1 is a schematic elevational view of one embodiment of the present invention.

Referring now to the drawing figures, wherein like numerals indicate similar elements throughout the views, FIG. 1 illustrates an in vitro fallopian tube device (IVFT) 10 for use in the fertilization of an ovum with sperm, and/or the development of an embryo for a period of time after fertilization. As would be contemplated and understood by those skilled in the industry, the present invention can be adapted for use with the ovum and sperm of any animal, including human ovum and sperm.

The IVFT 10 may include a chamber 12 having a tank 14 that is sized to hold a sufficient amount of fluid to assist in the fertilization of the ovum by the sperm and/or to assist in development of the embryo E. However, chamber 12 should be large enough to contain the container 30, which will be described in detail below, and have it immersed in fluid 22. Suitable examples of fluid levels to be held by tank 14 may include from about 10 ml to about 1000 ml. The chamber 12 may have a bottom, side walls, and a lid for sealing the tank 14 from outside conditions, and to minimize the possibilities of contaminants from entering the tank 14.

Chamber 12 and its various components can be made of any embryo compatible suitable material, particularly one that can be sterilized so that chamber 12 can be reused. Illustrative examples of suitable materials for chamber 12 include plastic, glass, metal or the like.

Chamber 12 may have at least one inlet port 16 to assist in establishing fluid communication with the reservoirs of fluid (e.g., 42). Inlet port 16 may be positioned adjacent to the bottom portion of the chamber 12 to assist in removing fluid 22 from within the tank 14 through an outlet 18 as additional fluid is added through the inlet 16. In addition, the chamber 12 also may have an outlet port 18, which is positioned adjacent the upper portion of the chamber 12, to assist in removing fluid 22 from the tank 14 as additional fluid is added through inlet port 16. This arrangement of the inlet port 16 and outlet port 18 can also assist in circulating fluid 22 in and around the tank 14, and around container 30 therein.

Chamber 12 may further be provided with a circulator 20 to assist in circulating (e.g., otherwise dispersing or disseminating, and preventing stagnation) the fluid 22 in tank 14. Circulator 20 can be provided in the tank 14 immersed in the fluid 22, or can be external to the tank 14 by gently moving or shifting the chamber 12 and thus, the fluid 22 within to achieve the desired circulation. Circulation of the fluid 22 in the tank 14 can assist in supplying an embryo E with nutrients (e.g., oxygen, amino acids and glucose) and removing metabolic wastes (e.g., urea, carbon dioxide, other metabolic waste) away from the embryo E. Circulator 20 can take the form of a programmable pump that can provide a steady flow or current of fluid 22, or a pulsating flow of fluid 22, as desired. Alternatively, a siphon or other apparatus or assembly to circulate fluid can be used with the present invention. Circulator 20 can be controlled manually with an on/off switch and preferably has a control switch or dial to adjust the rate of circulation, as desired. Alternatively, the circulator 20 can also be controlled by a feedback control system 90 and its CPU 96, as will be discussed later herein.

Inlet ports 16 can also have a one-way interface or valve that permits fluid 22 to flow from outside the chamber 12 (e.g., from connector line 48) to tank 14, but restricts or prohibits the flow of fluid 22 from inside the tank 14 back to the connector line 48. Likewise, the outlet port 18 can be fitted with a suitable one-way valve or interface to permit fluid 22 flow from the tank 14 out to the connector line (e.g., 64), but prohibits the backflow of fluid 22 into tank 14. Moreover, inlet port 16 and outlet port 18 may also be covered with a mesh filter (not illustrated) to prevent the outflow of an embryo E from tank 14. The mesh filter should have a suitably small pore size, such as around 75 microns for use with a human embryo, so that fluid 22, nutrients, and metabolic waste can easily flow through the mesh filter, but whereby, the embryo E cannot pass through the mesh filter.

The chamber 12 and its tank 14 are supplied with fluid 22 (e.g., media fluid I 24 and/or media fluid II 26) from the media supply system 40. Media supply system 40 provides tank 14 with sufficient supply of media or fluid 22 to assist in the fertilization of the ovum by sperm, and/or to assist in the development of an embryo E. A reservoir 42 for fluid can include one or more fluid supplies, such as bags of fluid, which can be hung or be suspended from an IV pole. The reservoir 42 can have several fluid release ports adjacent to the bottom of reservoir 42. For example, reservoir 42 can include an outlet port 45 and a testing port 44, each of which can include a seal 46. Testing port 44 assists in permitting the fluid (e.g., 24 or 26) within the reservoir 42 to be checked, such as for pH, prior to use with the present invention and for assisting in changing the contents of fluid (e.g., 24 or 26) therein. It is contemplated that the media supply system 40 of present invention may have a plurality of reservoirs 42 so that as one of the reservoirs 42 becomes empty, the other reservoir(s) (e.g. 42) can begin delivering fluid (e.g., 24 or 26) to the tank 14 while the other reservoir is being replaced or replenished.

Reservoir 42 may be coupled in fluid communication with tank 14 via a connector line 48 with an inner lumen 49. A connector 57, such as a hollow spike or piercing pin is preferably attached to, or formed at the proximal end 56 of the connector line 48 and can be inserted into and penetrate the seal 46 of outlet port 45. The distal end 58 of the connector line 48 is also preferably coupled in fluid communication with inlet port 16 of the chamber 12. Preferably, connector 57, such as a hollow spike or piercing pin, is attached to, or formed at the distal end 58 of the connector line 48 for connection (e.g., insertion into and penetration of) to the inlet port 16. The fluid communications or connections should preferably be air tight seals to reduce the possibility of contaminants entering the tank 14.

Connector line 48 can be of any length, and can be made of a soft plastic or other flexible material that provides a lumen 49 or passageway for fluid. Connector line 48 may be made of a transparent or translucent polyvinylchloride so the fluid flowing. through the connector line 48 is visible. In the present invention commonly used tubing in IV systems can be used as connector line 48. The material of connector line 48 may also allow fluid 22 within the lumen 49 to be heated or cooled, as desired. As with chamber 12, connection lines 48 and 64 can be made of a material that can be sterilized for reuse.

Fluid flow from the reservoir 42 to the tank 14 may be selectively metered or controlled, as desired. A valve or flow control member 50 can be provided along connector line 48 between the reservoir 42 and chamber 12 to selectively control the rate of fluid flow or discharge from the reservoir 42. Suitable examples of flow control members 50 can include a line clamp, thumb wheel or roll clamp, a pinch clamp, snap-lock sclamp, screw clamp, side clamp or other devices known to those skilled in the industry.

Flow control member 50 can take the form of an electronically controlled valve, which can be electrically connected to the feedback control system 90 via line 51, as will be discussed later herein for opening, closing, or otherwise selectively regulating fluid flow through the lumen 49. Hydrostatic pressure can be used to assist in draining or pushing fluid 22 from the reservoir 42 to the tank 14 if the reservoir 42 is elevated at a desired distance above chamber 12, and preferably above inlet port 16.

It is further contemplated that a pump 52 may also be provided along connector line 48, or around the reservoir 42, to assist in selectively moving fluid 22 from the reservoir 42 to the tank 14. Pump 52 can be selectively controlled manually with an on/off switch, and preferably has a control mechanism to vary the fluid flow rate through the connector line 48, as desired. Pump 52 can also be electrically connected to the feedback control system 90 via line 53, to automatically control fluid flaw rate, as desired.

Moreover, it is preferable to selectively maintain and/or regulate the temperature in the chamber 12. More specifically, the temperature of fluid 22 within tank 14 should be selectively regulated to provide an optimal temperature for fertilization and/or embryo growth. The chamber 12 can be selectively directly heated (and/or cooled) by immersion in a liquid bath to heat (or cool) the fluid 22, as desired. Fluid 22 from the reservoir 42 may also be selectively heated (and/or cooled) as it travels or flows to the tank 14 through the connector line 48. A sufficient portion of connector line 48 may be immersed in a temperature regulator 54, such as a warm bath or heater, having a constant or variable temperature to bring the fluid 22 from room or ambient temperature up to the optimal temperature. The temperature can be regulated, depending on the type of embryo being fertilized or developed (e.g., sheep, cow, horse, mouse, or others). In humans, the desired temperature for embryo E development is from about 96° F. to about 100° F. (about 35.5° C. to about 37.7° C.), more preferably between about 97° F. and 99° F., and most preferably about 98.6° F. (about 37° C.). Temperature regulator 54 can be controlled with an on/off switch, and temperature regulator 54 can include a thermostat to assist in regulating the temperature of the temperature regulator 54, as desired. Alternatively, temperature regulator 54 can also be electrically connected via line 55 to and controlled by the feedback control system 90.

The IVFT 10 also includes a collection system 60 to collect fluid 22 from the tank 14 as it is being discharged and/or replaced. A reservoir 62 to collect the discharge fluid 22 is in fluid communication with the tank 14 through a connector line 64. Reservoir 62 can be any type of fluid collection container, such as a jar, a can, or a bag that expands when filled with fluid. Connector line 64 can be any type of piping or tubing, similar to connector line 48.

A container 30 can be provided within tank 14 to house or otherwise contain the embryo E or embryos within the tank 14. It is also contemplated that multiple containers 30, each containing an embryo E, can be provided within one tank 14. Also, container 30 can be provided to assist in the fertilization of the ovum by a sperm. Container 30 can take the form of any desired receptacle, including a rectangular or square shaped box with a plurality of walls 32, a frustoconical shaped beaker, or a cylindrical tube. Container 30 may be made of a material that assists in the flow of fluid 22 within the container 30 to provide nutrients (e.g., glucose, amino acids and oxygen) to the developing embryo E, and assists in the removal of metabolic waste, including urea and carbon dioxide, away from the embryo E. Suitable material for the container 30 and its walls 32 may include a microporous material and preferably a embryo compatible material.

Container 30 may also have a lid 34 made of a material that permits fluid, nutrients and waste products to flow therethrough (e.g., a microporous material). The lid 34 can be affixed to the container 30 at its top. Suitable examples of attachment means include a screw-on lid, a snap-on mechanism whereby a lip on the inner surface of lid 34 snaps around a lip on the outer surface of wall 32, or another attachment or sealing assembly known in the art.

The walls 32 of container 30 may be provided with one or more windows 36 so that fertilization of the ovum by the sperm, and/or development of the embryo E can be monitored without physically manipulating the ovum, sperm and/or embryo E. Window 36 preferably should be transparent so that a viewing device (e.g., 86) of visualization assembly 70 or the eye can view the fertilization and/or development of embryo E inside container 30. Also, windows 36 should also be translucent so that the inside of the container can be lit or illuminated, such as by backlighting it with a light source 72 outside of the container 30 (preferably a cool light source which will not elevate the temperature within container 30). The windows 36 should be sufficiently sized so that the embryo E can be monitored without physical manipulation, such as by using the visualization assembly 70, yet not so large that they adversely affect fluid flow in and through container 30.

Figure 2:
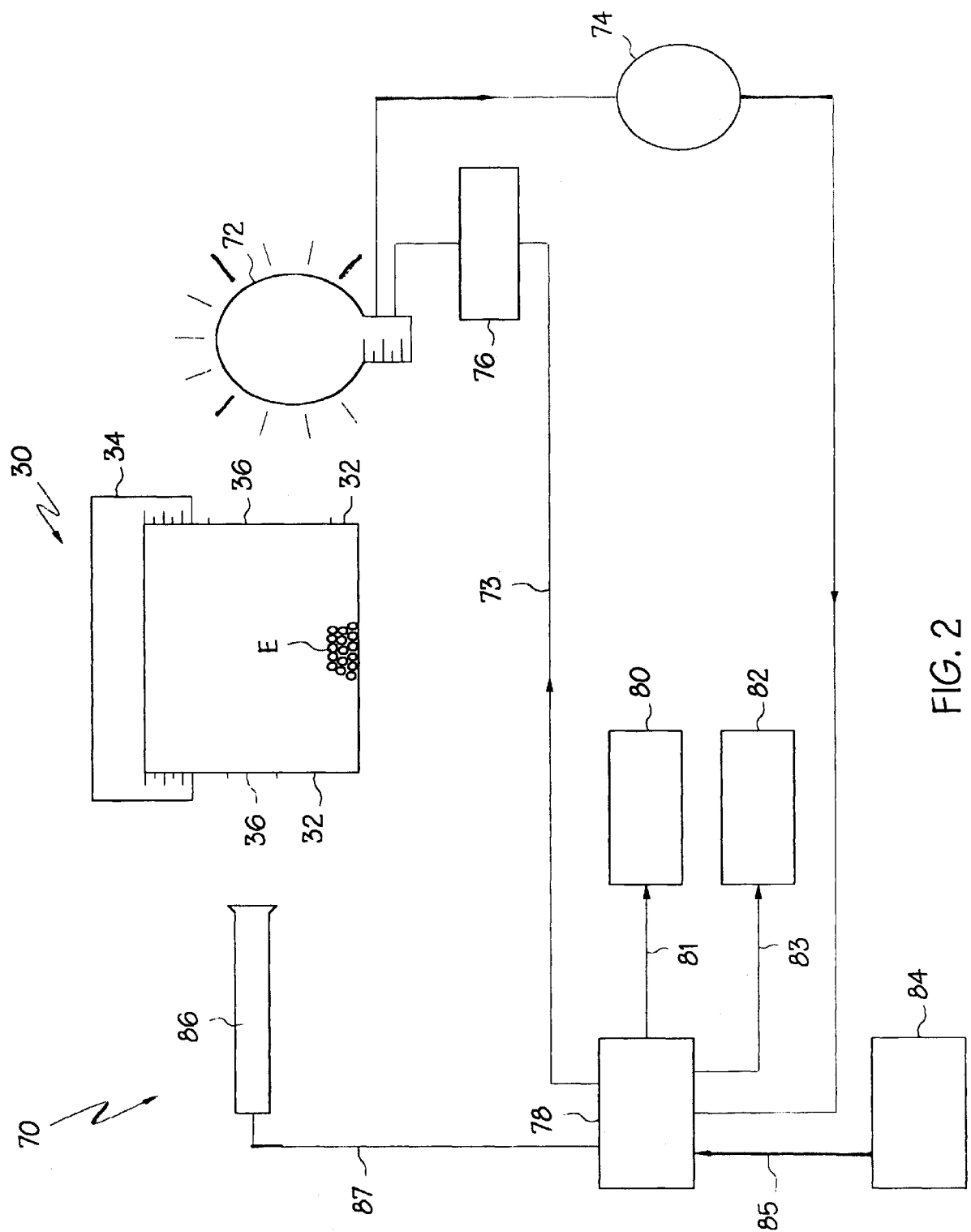
FIG. 2 is a schematic elevational view of one embodiment of a visualization assembly according to the present invention.

As mentioned above, the present invention preferably includes a visualization assembly 70, as best illustrated in FIG. 2, so that the fertilization of the ovum by the sperm, and/or development of the embryo E can be observed (e.g., monitored, examined, recorded, and/or viewed) without the need for physically manipulating the contents. The visualization assembly 70 may permit sequential and continuous observation of the embryo E. It is contemplated that the visualization assembly can assist in studying and predicting which embryo will result in a successful pregnancy.

The visualization assembly 70 can include a viewing device 86, such as a lens or other magnification device, and/or a photodocumentation device (such as a camera) which can be placed adjacent one of the windows 36 of container 30 for observing (e.g., monitoring, examining, recording, or viewing) the inside of the container 30. Viewing device 86 can also be placed inside the container 30. The viewing device 86 can be a still shot camera, a video recorder, a microscope lens or the like. Preferably, viewing device 86 has an adjustable magnification unit which can allow for panoramic views of the contents and/or close-up views of the contents of container 30, as desired. The viewing device 86 can be electrically connected to a display device 80, such as a television, computer screen, monitor or the like, so that the developments within the container 30 can be viewed at a site away from or remote from the device 10.

Viewing device 86 can also be electrically connected to a computer or microprocessor, such as microprocessor 78 via line 87. The images viewed or recorded by viewing device 86 can be captured and stored, preferably in a digital format, by the microprocessor 78 so that they can be enhanced, stored, and/or recalled at a later date, as desired. The microprocessor 78 can also be electrically connected to a display device 80 via line 81 so that the image(s) can also be viewed at a site remote from the chamber 12. Controller 84 can be electronically connected to the microprocessor 78 via line 85 so that the operations of viewing device 86, display 80 and/or a printer 82 (as will be discussed below) can be monitored, controlled and/or changed by an operator. Controller 84 can take the form of a keyboard, disk drive, CD-Rom drive, display touch screen, or a like device for the input of data or controls. As alluded to above, a printer 82 may be electrically connected to the microprocessor 78 via line 83 so that still shots or images captured by viewing device 86 can be reproduced on photographic paper or other type paper used with the printer 82.

Visualization assembly 70 may also include a mechanism to illuminate or light the inside of container 30 so that images therein can be viewed and/or recorded. a light source or other illumination device 72 may be provided outside of container 30 so that light from light source 72 can illuminate the inside of the container 30 through one of the windows 36. It is contemplated that a light source 72 could also be provided inside the container 30 to assist in lighting or illuminating the contents therein. Light source 72 may have an on/off switch and may have a rheostat 76 so that the intensity of light given off by the light source 72 can be controlled by varying electrical current therethrough. Light source 72 may be electrically connected to the microprocessor 78 via a line 73 so that the operations of the light source 72 (e.g., on, off, and/or intensity) can be controlled by the CPU, either automatically, or by the controller 84.

Figure 3:
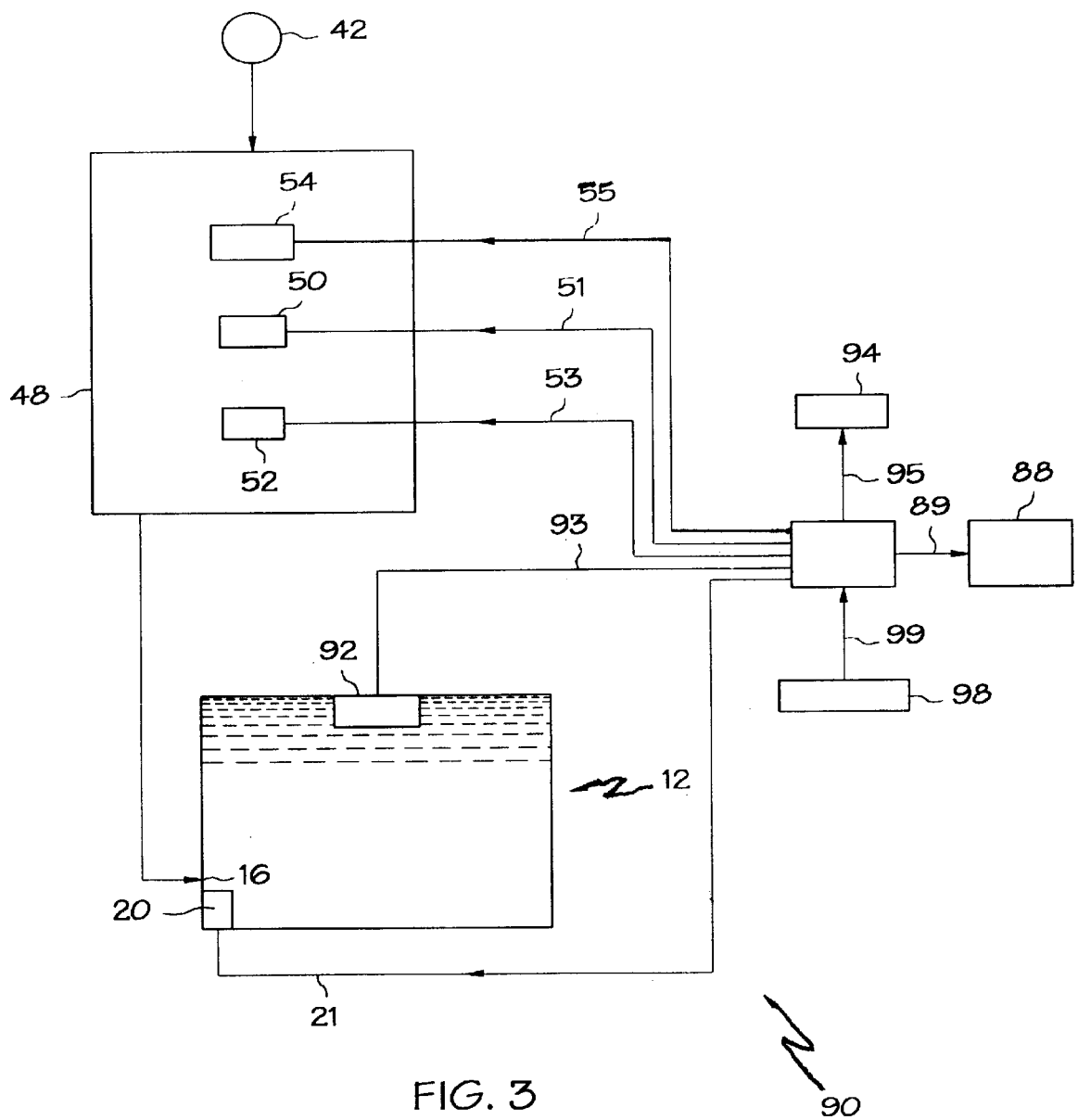
FIG. 3 is a schematic elevational view of one embodiment of a control system according to the present invention.
Figure 4:
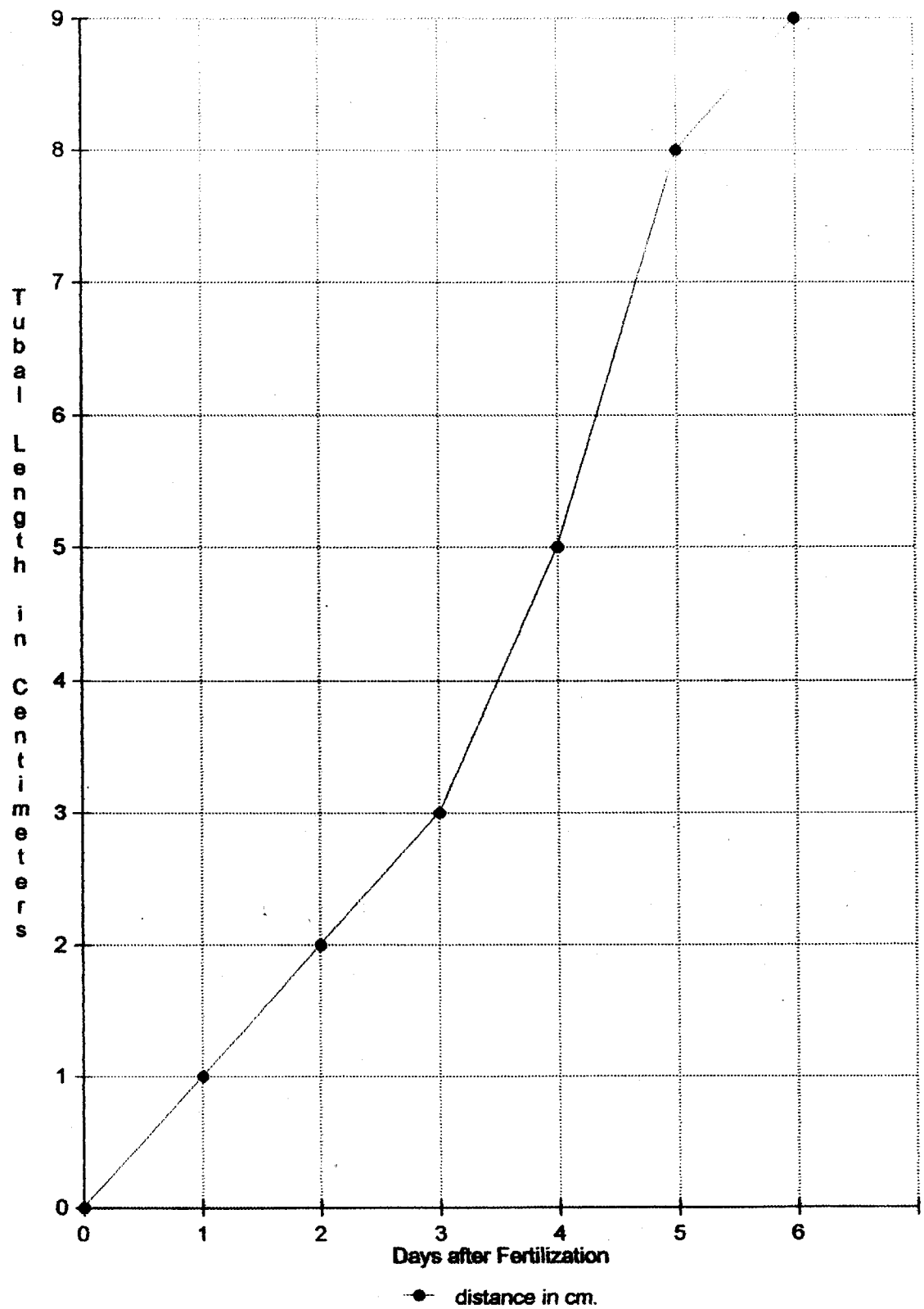
FIG. 4 is a two-axis chart plotting embryo transit in distance traveled per day vs. the number of days post fertilization.
Figure 5:
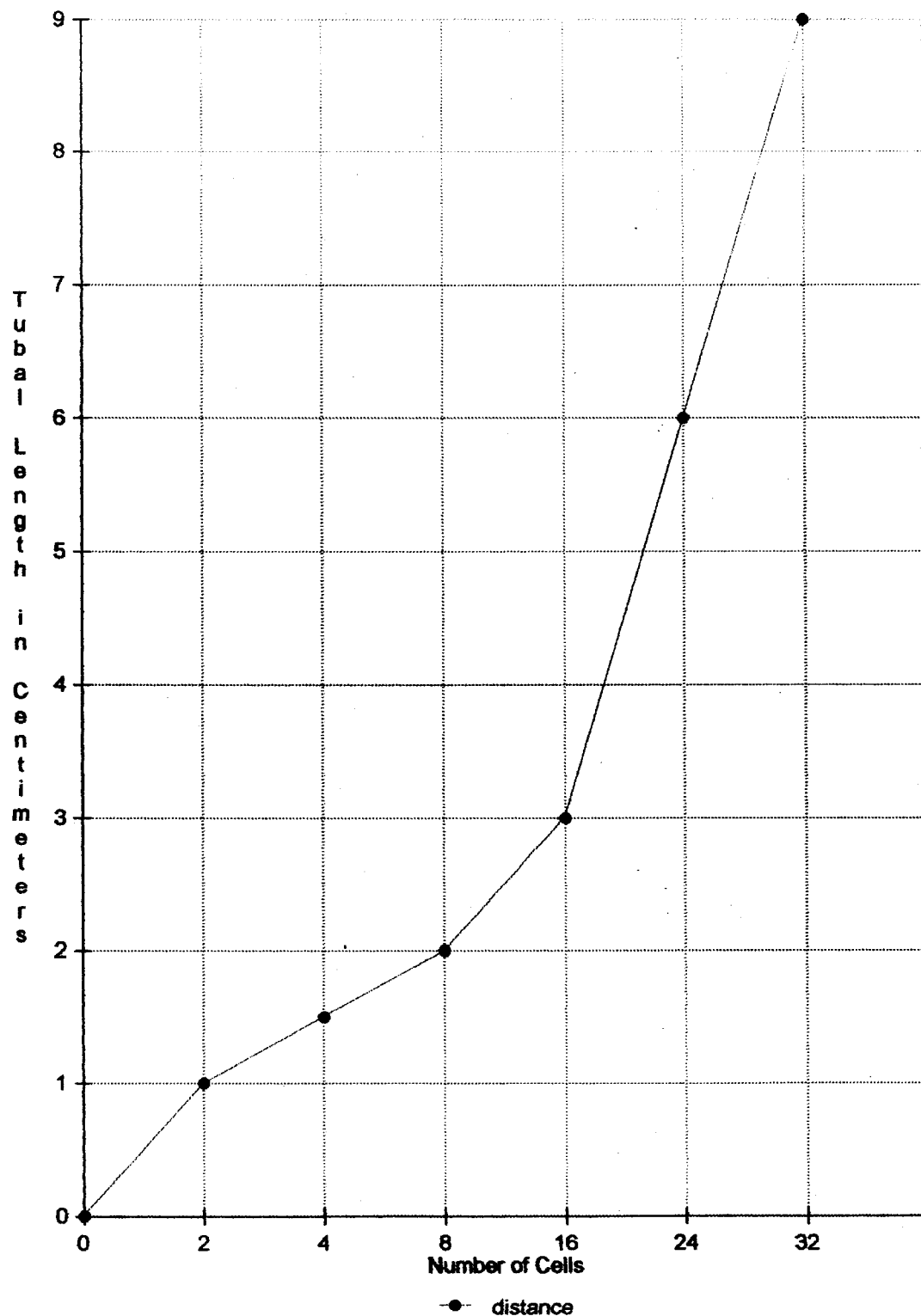
FIG. 5 is a two-axis chart plotting embryo transit in distance traveled per day vs. the number of cells of the embryo.
Figure 6:
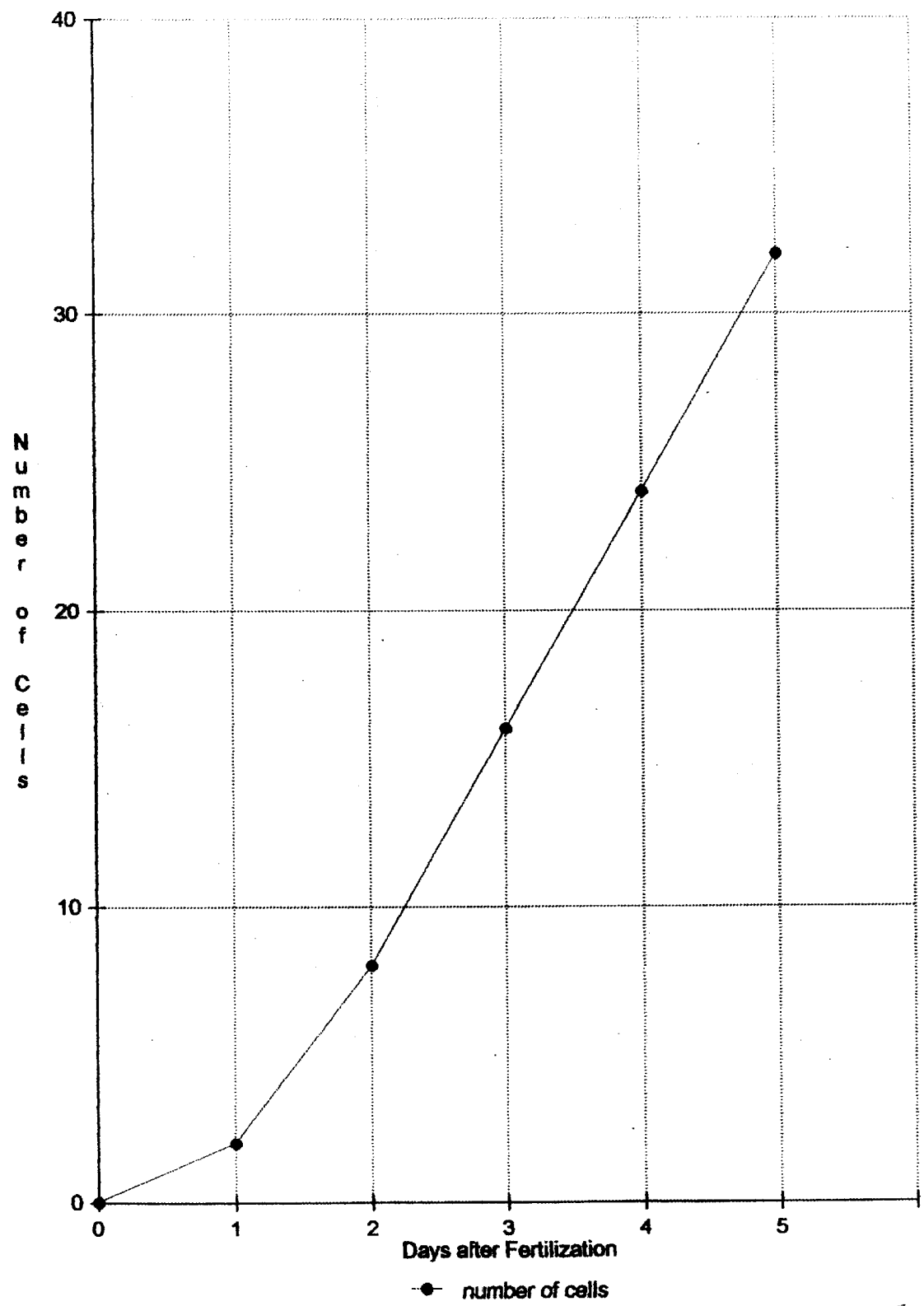
FIG. 6 is a two-axis chart plotting the number of cells of the embryo per day vs. the number of days post fertilization.

The present invention, as best illustrated in FIG. 3, may also comprise a feedback control system 90 for monitoring and/or changing the conditions in tank 14 to provide optimal fertilization and/or development conditions. The feedback control system 90 can include a sensor system 92 that can be provided within the tank 14 to monitor the conditions of the fluid or media 22. A variety of different types of sensors may be used with the sensor system of the present invention, such as a pH sensor 92A to monitor pH conditions in the tank 14, an oxygen sensor 92B to monitor the oxygen level in the tank 14, a carbon dioxide sensor 92C to monitor the carbon dioxide level in the tank 14, and/or a thermometer 92D to monitor temperatures in the tank 14. These sensors (e.g., 92A–D) can assist in monitoring the level of nutrients (e.g., amino acids, glucose and oxygen) within the fluid or media 22 in the tank 14, as well as the metabolic waste, such as urea and carbon dioxide. Each specific sensor may have its own display or readout device so that a quantitative measure of the conditions within the tank 14 may be displayed. The sensors of the sensor system 92 can be either an analog type or preferably a digital type, which can be generally more accurate.

The sensor system 92 may also be electrically connected to a microprocessor 96 (microprocessor 96 and microprocessor 78 may be one central processing unit) via line 93 or have a microprocessor built in. The microprocessor 96 may include a control feedback loop program, and use the information gathered by the sensor system 92 to control the rate, frequency, and fluid flow from the reservoir 42 to the tank 14 via connector line 48, to control the circulation rate of fluid in the tank 14, and/or to control the temperature of fluid in the tank 14 and lumen 49. Various alarm levels, preferably conditions that are outside preferred or optimal development conditions, can be set for the variables or conditions being monitored.

For example, if the temperature of media 22 within tank 14 drops below a desired level, additional warmer fluid 22 may be added to the tank 14 by providing fluid from the reservoir 42 that has been heated by temperature regulator 54 along connector line 48.

As another example, if the urea concentration within the fluid or media 22 of tank 14 rises beyond the desired or alarm level, fluid 22 may be automatically removed from the tank 14 through the outlet port 18 by adding additional fluid 22 from the reservoir 42 through inlet port 16.

The control feedback system 90 may further comprise a clock 101. Clock 101 can be used to track the time post fertilization, which may be used as an indicator to change fluid 22 in the tank 14. At specifically predefined intervals after fertilization, the embryo E will have different nutritional needs as it develops and changes. As such, it may be necessary to replace the fluid media 22 within tank 14 with a different media supply. Clock 101 may also be electrically connected to the valve 50 via a line 51, the pump 52 via line 53, the heater 54 via line 55 or the circulator 20 via line 21.

At the specific predefined intervals, the fluid 22 may be exchanged within the tank 14, and circulated, as desired.

Fluid 22 can be any type of media or solution that is used with in vitro fertilization of the ovum by sperm. Fluid 24 can be any type of media or solution that is used to assist in the development of an embryo during the period immediately following fertilization up until about 2 days post fertilization. Illustrative examples of such fluids can include standard media with or without the addition of about 10% human serum. As the nutritional requirements of the embryo changes, different fluid (e.g., 26) may be used with the present invention to meet those requirements. Fluids used on day three after fertilization and thereafter may be enriched with carbohydrates or amino acids.

In use, an in vitro fallopian tube device 10 can be used to assist in the fertilization of an ovum by sperm, and/or to assist in the development of an embryo E until it is inserted or implanted into a female. An ovum follicle is preferably removed from an ovary prior to eruption using tools and equipment known in the industry, such as a celioscopy. The sperm can likewise be gathered from a male and can be treated, as desired, to remove immobile or dead sperm or other cells that can interfere with the interaction of the sperm with the ovum.

Once the sperm and ovum have been collected, they can be placed in close proximately to each other so as to enhance the chances or possibility of fertilization. Fertilization can occur in the container 30 of the present invention with fluid or a media solution 22 in tank 14, or outside the device 10, such as in a petri dish. When fertilization occurs outside the device 10, the resulting embryo E is transferred to the container 30 soon after fertilization using standard transporting techniques and equipment.

Tank 14 may be initially filled with a fluid or media 22 that assists in the development of the embryo E, preferably prior to insertion of the ovum and sperm, or the embryo. Fluid 22 within the tank 14 of ovulation 20 can be circulated by circulator 20 to assist in providing nutrients (e.g., amino acids, glucose and oxygen) to the developing embryo as well as assist in the removal of waste products such as urea and carbon dioxide from the developing embryo E. Circulator 20 can either be selectively manually controlled with an on/off switch and/or control valve to regulate the circulation as desired. Circulation of the media within tank 14 can either be at a steady state flow of the fluid 22 in tank 14, or in a pulsating flow.

While the embryo E is developing, conditions within the tank 14 can be monitored by the sensor system 92. Conditions that may be monitored by the sensor system 92 and its various sensors (e.g., 92A–D) can include the pH of the fluid 22, the temperature, the oxygen level of the fluid 22, the carbon dioxide level of the fluid 22 and other conditions, as desired. Quantitative measures of these conditions of the fluid 22 in the tank 14 can be displayed on a display 94. The signals being generated by the sensor system 92 can also be electronically transmitted on line 93 to the microprocessor 96, whereby the signals can be compared to alarm levels, and/or displayed on a display device 94. Data transmission of the signals along lines 93 and 95 may be constant, or at predefined intervals, such as every five minutes or the like.

The time after fertilization can also be maintained and displayed on the display 94 either by a clock 101 or microprocessor 96.

At about 24 hours after fertilization, the fluid 22 within the tank 14 may be exchanged or replaced. Fluid from the reservoir 42 is pumped or otherwise flows through the connector line 48 and its lumen 49, such as by opening valve 50 and/or turning on pump 52, as desired. Fluid can enter the tank 14 through inlet 16. Fluid that is within the tank 14 exists through outlet 18 and flows through a connector line 64 to reservoir 62, which is part of the collection system 60. Fluid can be replaced at predefined intervals so as to remove waste products from the tank 14, and to provide the tank 14 with additional nutrients to assist in the development of the embryo E. The exchange of fluid 22 can be done manually by an operator, or by the microprocessor 96 sending instructions to the valve 50 to open and how much to open via line 51, to the pump 52 to assist in moving fluid through the lumen 49, and to the temperature regulator 54 to heat or cool the connector line 48 and the fluid therein. In addition, the microprocessor 96 can send instructions to the circulator 20 to circulate fluid 22 within the tank 14, and specifically, the rate of circulator.

In one embodiment, fluid 22 within the tank 14 is exchanged or replaced at about 24 hours after fertilization and then again at about 48 hours after fertilization. Replacement of the fluid 22 may be accomplished each time using the same procedures, as described above. As the embryo increases in cell mass and moves from the zygote to the blastocyst stage, it is contemplated that the exchange of fluid or media 22 would need to occur more frequently than every 24 hours. Starting at day 3 after fertilization, a different media solution (e.g., fluid 26 instead of fluid 24) is provided to the developing embryo E, since its nutritional requirements have changed as it has developed. This media solution 26 may have a higher level or concentration of glucose and amino acids. During day 3 after fertilization, the fluid 22 in tank 14 may be exchanged or replaced approximately every 12 hours. During day 4 after fertilization, the fluid 22 in tank 14 is again exchanged or replaced periodically, such as about every 8 hours, to remove waste products and provide additional nutrients for the development of the embryo E. During day 5 after fertilization, the fluid 22 in tank 14 is exchanged or replaced again at a predefined frequency, such as about every 6 hours, to remove waste products produced by the embryo E and provide additional nutrients for its development.

Since all living things develop at different rates, it is contemplated that each embryo E will develop at a different rate. In order to assist in providing an optimal development condition for the embryo E, the sensor system 92 can monitor the condition of the fluid 22 within the tank 14. Signals can be constantly or periodically (e.g., about every five minutes) sent to the microprocessor 96 via line 93. These signals can be compared with alarm levels set by the operator, and in the control feedback loop program. If the microprocessor 96 (control loop feedback program) or an operator determines that the media 22 has changed, that is, it has either risen above or fallen below an alarm level, the operator or microprocessor 96 may automatically change fluid 22 in tank 14, as detailed with the steps above. For example, if the embryo E is developing at a faster than normal or expected rate, it may have increased nutritional requirements and thus, will produce additional waste products. When either the low nutritional level of the fluid 22 is reached and detected by the sensor system 92, or the increased waste level of the fluid 22 is reached and detected by the sensor system 92, the signal sent to the microprocessor 96 can be compared with alarm levels set in the control feedback loop program to detect this condition in the fluid 22 via sensor system 92. In response to this condition, the microprocessor 96 may automatically send a signal through line 51 to valve 50 opening it and also send and electrical signal through line 53 to pump 52 so that new media (e.g., 24 or 26) is selectively moved from reservoir 42 through connector line 48 to tank 14. In response to increase fluid level in the tank 14, the existing fluid 22 within the tank 14 flows out of the tank 14 through outlet port 18 and into the reservoir 62 through connector 64.

As the embryo E develops and more cells are formed, it is contemplated that the circulation rate of fluid 22 within tank 14 will be increased to assist in the development of the embryo E. This adjustment of circulator 22 can either be manually done, or automatically done by the microprocessor 96 by sending an electrical signal through line 21 to the circulator 20.

The present invention, as mentioned above, is also provided with a visualization assembly 70 which can permit the development of the embryo E to be observed (e.g., monitored, viewed, recorded, etc.) without manipulating or otherwise moving the embryo E. The developmental progress of the embryo E can be monitored by viewing the embryo E on a display 80 in real time as images are being recorded with a viewing device 86 through window 36 in the container 30. Other measurements of the embryo E can be gathered, such as number of cells, volume of the embryo, growth rate over a period of time. This information can be used to predict whether the embryo E will result in a successful pregnancy. The container 30 may be back lit using a light source 72, which illuminates the interior of container 30 through another window 36 that may be provided, for example, in the wall 32 of the container 30. The image of the developing embryo E may be recorded by viewing device 86, and can be also electronically transmitted via line 87 to the microprocessor 78 for storage as a file, manipulation, or recall at a later date. It is also contemplated that a stored image from the microprocessor 78 or a current image being viewed lens 86 can be printed on a printer 82 by sending an electrical signal through line 83 from the microprocessor 78 to the printer 82. The visualization assembly 70 can also be changed, modified, updated, the like using a controller 84 to give the visualization assembly 70 instructions. For example, images can be recalled from the microprocessor 78, viewed on display 80, and printed on the printer 82.

Once the embryo has sufficiently developed to the appropriate stage, it can be determined whether a successful pregnancy would result, based in part of the progress of the embryo. If a determination is made not to implant the embryo into a female, the procedure can be terminated.

If the embryo is to be implanted into a female, the fluid 22 in the tank 14 would be exchanged or replaced. The lid 34 would be removed from the container 30. A transfer catheter or other device known in the art can be used to secure the embryo E. Embryo E can thereafter be inserted into the uterus, and preferably into the anterior portion of the uterus, where the endometrium is richer and more developed. The embryo E may also be transferred to an implant balloon, such as the device disclosed in U.S. Pat. No. 5,961,444, filed Oct. 17, 1997 entitled, "In Vitro Fertilization Procedure Using Direct Vision," the disclosure of which is hereby incorporated herein by reference. Thereafter, the balloon and embryo E are inserted into the uterus, and the balloon inflated. Thereafter, the embryo implants into the uterus.

Figure 7:
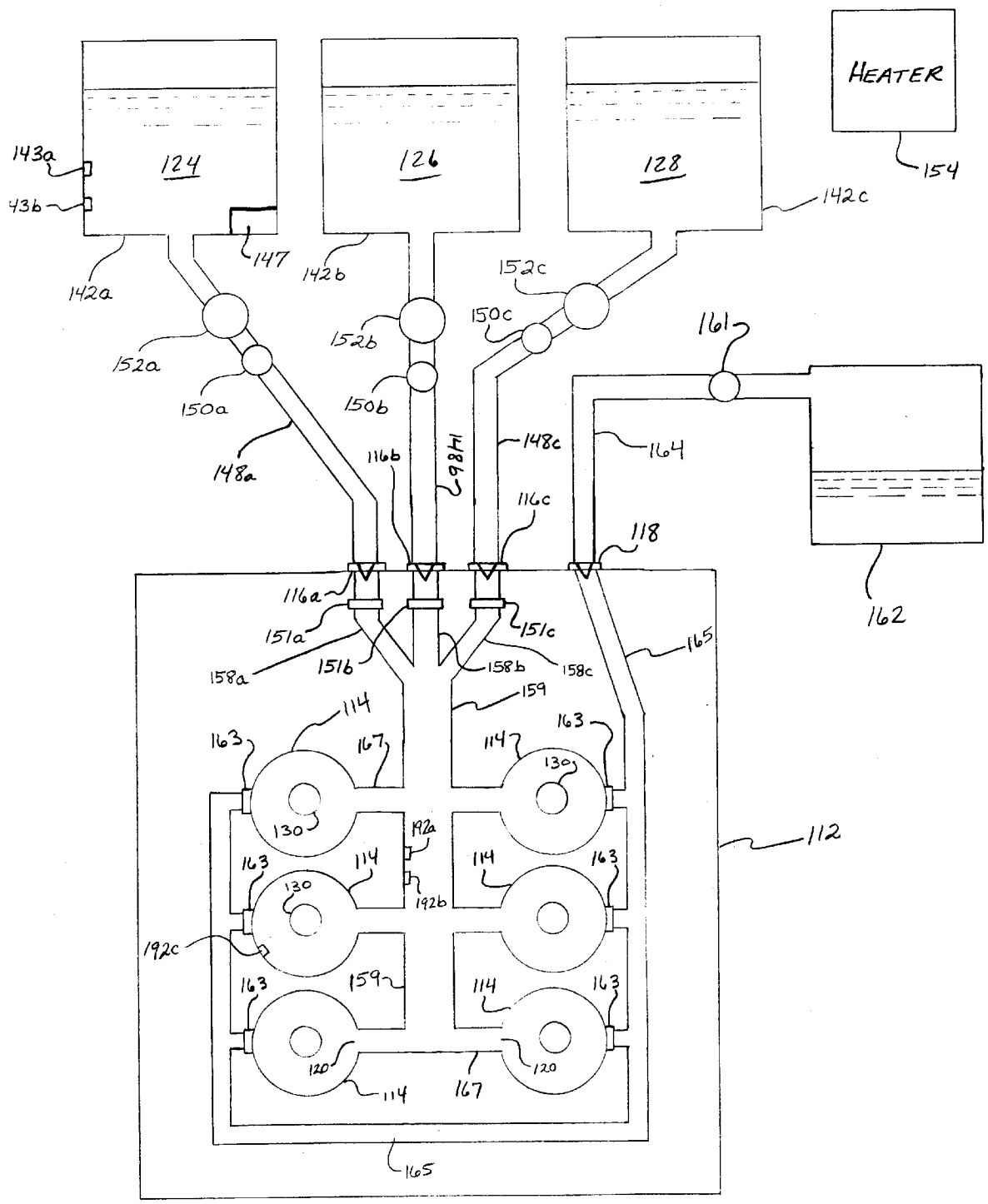
FIG. 7 is a schematic illustration of an alternative embodiment for an IVFT device according to the present invention.

FIG. 7 is a schematic illustration of an alternative embodiment of an IVFT device according to the present invention, wherein a closed system is provided wherein each embryo may grow without being manipulated or moved from one container to another (even when the fluid growth media is changed). It will be understood that certain features of the embodiment of the IVFT device of FIG. 7 have been omitted for purposes of clarity, and are depicted in other figures (as further described herein). In the embodiment of FIG. 7, the chamber of the IVFT device comprises a cartridge 112 which includes one or more embryo growth tanks 114 therein. Each tank 114 is sized to accommodate a growing embryo and a sufficient amount of fluid media to allow for the fertilization of an egg and/or the development of an embryo therein. In one embodiment, therefore, each tank 114 may have an internal volume of between about 50 and about 1000 ml. In the embodiment shown in FIG. 7, cartridge 112 includes six embryo growth tanks 114, however any number of growth tanks 114 may be provided in a single cartridge (including a single tank).

As was the case in the previously-described embodiments, each embryo growth tank 114 may include a container in which the embryo is located, namely embryo well 130. Embryo well 130 may comprise a discrete compartment within embryo growth tank 114. Alternatively, in the embodiment of FIG. 7, embryo well 130 essentially comprises the lower portion of embryo growth tank 114 (see, e.g., FIG. 9, and as further described below). Each embryo container (or well) 130 may be sized and configured for retaining a growing embryo therein. When embryo well 130 comprises the lowermost region of embryo growth tank 114, a growing embryo may be retained within well 130 due to gravitational forces. It will be understood, however, that a separate container or region (i.e., embryo well 130) need not be provided within each embryo growth tank 114. Thus, the growing embryo resides within embryo growth tank 114, and may optionally be located within a container or other discrete region of the growth tank (such as well 130).

Cartridge 112 is configured so that it may be placed in fluid communication with one or more sources of fluid media. Thus, as shown in FIG. 7, first, second and third media reservoirs 142a, 142b, and 142c, respectively, are located in fluid communication with cartridge 112, via fluid media inlet lines 148a, 148b and 148c, respectively. In this manner, fluid media contained within each of the media reservoirs 142a, 142b and 142c may be provided to cartridge 112. While fluid from reservoirs 142 may be gravity-fed to cartridge 112, fluid is preferably pumped into cartridge 112. Thus, a media pump 152 and a media valve 150 may be provided along each media inlet line 148, such that fluid media from each reservoir 142 may be selectively urged into cartridge 112 by means of pump 152. The flow rate and pressure of the fluid media provided to cartridge 112 may be further regulated by a media valve 150.

As yet another alternative to employing pumps 152 for urging fluid media into cartridge 112, fluid media reservoirs 142 may each be pressurized with $CO_2$. By pressurizing the fluid media reservoirs with $CO_2$ (or other suitable gas), gas pressure may be employed to urge fluid media from each reservoir 142 into cartridge 112. In. addition, pressurizing each media reservoir 142 with $CO_2$ will assist in maintaining the proper fluid pH (preferably between about 7.2 and about 7.4 for human embryos, more preferably about 7.3±0.5). A separate $CO_2$ tank may be provided in the IVFT device, along with suitable connection lines for directing $CO_2$ gas into each of the fluid media reservoirs 142. Each of the connector lines may also include a valve therein for controlling the pressure and amount of $CO_2$ delivered to each of the fluid media reservoirs 142. In addition, such $CO_2$ valves may even be controlled by means of the control system described further herein. Pressure monitors may also be provided within the $CO_2$ tank, and optionally along each of the $CO_2$ connector lines, in order to monitor gas pressure, as well as to provide such data to the CPU of the control system (as further described herein). A pH monitor may similarly be provided in each reservoir 142 to monitor the pH of the fluid therein.

Each media reservoir 142 is configured to accommodate a fluid media. Thus, media reservoir 142a is depicted housing first fluid media 124, media reservoir 142b housing second fluid media 126, and media reservoir 142c housing third fluid media 128. Of course it will be understood that any number of media reservoirs 142 may be provided, and the use of three separate fluid media reservoirs, as shown in FIG. 7, is merely exemplary of one embodiment of the present invention.

By providing separate inlet lines 148, along with separate pumps 152 and valves 150 for each fluid media, the type, flow rate and pressure of fluid media provided to cartridge 112 may be controlled as desired. For example, during fertilization or the initial stage of embryo development, first fluid media 124 may be urged into cartridge 112 (i.e, pumps 152b and 152c, and/or valves 150b and 150c may be turned off and/or closed, respectively). After a predetermined period of time, or after a predetermined amount of embryo growth has been observed, pump 152a and/or valve 150a may be turned off and/or closed, respectively. At the same time, pump 152b and valve 150b may be turned on and opened, respectively, thereby delivering second fluid media 126 to cartridge 112. Similarly, after another predetermined period of time, or a predetermined amount of embryo growth has been observed, the delivery of second fluid media to cartridge 112 may be stopped (such as by turning off pump 152b and closing valve 150b), and the delivery of third fluid media 128 to cartridge 112 may simultaneously commence (such as by turning on pump 152c and opening valve 150c).

As an alternative to sequentially providing first, second, and third fluid media 124, 126 and 128 to cartridge 112, any of a variety of combinations of first, second and third fluid media may be delivered to cartridge 112, as desired. For example, instead of abruptly switching from first fluid media 124 to second fluid media 126, pumps 152a and 152b, along with valves 150a and 150b, may be controlled in order to gradually decrease the amount of first fluid media 124 delivered to cartridge 112, while simultaneously increasing the amount of second fluid media 126 delivered to cartridge 112. In this manner, the fluid media surrounding the growing embryos within cartridge 112 may be gradually changed from one fluid media to another. In addition, the fluid media surrounding embryos in cartridge 112 may be tailored in response to certain indicia of embryonic growth and health (such the growth rate of an embryo, or the levels of embryonic waste products such as urea). For example, first, second and third fluid media 124, 126 and 128, respectively, may be simultaneously delivered to cartridge 112 in varying proportions. In this manner, the composition of the fluid surrounding an embryo within cartridge 112 may be precisely tailored in accordance with a predetermined schedule, or in response to embryo growth data (e.g., the number of cells, or waste production data).

Cartridge 112 is further configured so that it may be placed in fluid communication with a fluid waste reservoir 162. A fluid discharge line 164 allows fluid media leaving cartridge 112 to be directed to waste reservoir 162 for storage and later disposal. A valve 161 may be provided on discharge line 164 in order to regulate the flow of waste fluid media into waste reservoir 162. Although a pump or other suitable device may be provided for removing waste fluid media from cartridge 112, in the embodiment of FIG. 7 fluid media entering cartridge 112 through one or more of media inlet lines 148a, 148b and 148c will displace fluid media already in cartridge 112, thereby urging waste fluid out of cartridge 112 and into waste reservoir 162. Such fluid displacement will readily occur, since it is preferred that the entire volume of each tank 114 is fluid filled (i.e., no air space in tanks).

In the embodiment shown in FIG. 7, one end of cartridge 112 includes fluid inlet ports 116a, 116b and 116c. Fluid inlet ports 116 are configured such that cartridge 112 may be placed in fluid communication with fluid media inlet lines 148. Preferably fluid inlet ports 116, as well as fluid inlet lines 148, are configured such that cartridge 112 may be put in fluid communication with fluid inlet lines 148 in a non-permanent manner. In other words, cartridge 112 is configured such that it may be separated from fluid media inlet lines 148, as desired. In addition, inlet ports 116, as well as outlet port 118 (described below) may be configured to allow fluid flow in only one direction (into or out of cartridge 112). By way of example, hollow spike connectors or piercing pins, as described previously, may be provided at the end of each fluid media inlet line 148, and each fluid media inlet port 116 on cartridge 112 may be configured for non-permanent attachment to these hollow spike connectors in the manner described previously. Of course other suitable connectors well-known to those skilled in the art, and corresponding fluid port assemblies, may be used.

Each fluid media inlet port 116, is in fluid communication with a separate cartridge feed line 158. Thus, fluid media inlet port 116a is in fluid communication with cartridge fluid feed line 158a, media inlet port 116b is in fluid communication with cartridge feed line 158b, and inlet port 116c is in fluid communication with cartridge feed line 158c. In the embodiment shown, each of the three cartridge feed lines 158a, 158b and 158c is also in fluid communication with main cartridge fluid line 159 (as best seen in FIG. 7). In this manner, fluid media entering cartridge 112 from one or more of media reservoirs 142a, 142b or 142c is directed into main cartridge fluid line 159. Alternatively, fluid may be directed from media inlet lines 148 separately into each tank 114.

Each embryo growth tank 114 in cartridge 112 is in fluid communication with main fluid line 159, such that fluid media is directed into each of the individual embryo growth tanks 114. Cartridge 112 further includes a cartridge fluid discharge line 165 which is in fluid communication with waste fluid outlet port 118. Fluid outlet port 118 may be configured similarly to fluid inlet ports 116 on cartridge 112, such that cartridge 112 may also be non-permanently placed into fluid communication with a waste discharge line 164, thereby allowing waste fluid to be discharged into waste reservoir 162. Each of the embryo growth tanks 114 is also in fluid communication with cartridge fluid discharge line 165, such that fluid leaving each embryo growth tank 114 will be discharged into waste reservoir 162 through cartridge discharge line 165 and waste discharge line 164.

In order to further regulate fluid flow within cartridge 112, as well as fluid pressure, one or more valves may be provided on the various fluid lines in cartridge 112. Thus, as shown in FIG. 7, fluid media valves 151a, 151b and 151c may be provided on cartridge feed lines 158a, 158b and 158c, respectively. In addition, discharge valves 163 may be provided at the fluid outlet from each embryo growth tank 114, or on cartridge discharge line 165 downstream from the fluid outlet of each embryo growth tank 114, in order to regulate the discharge of fluid from growth tanks 114. In this manner, the flow of fluid into and out of each embryo growth tank 114 can be precisely regulated, as desired. In addition, the fluid pressure within each embryo growth tank can also be modified as needed (such as maintaining a constant fluid pressure which differs from the atmospheric pressure, particularly when the device is used at an altitude significantly above or below sea level). In addition, fluid pressure within each tank 114 may be increased as the embryo develops. It should also be noted that the IVFT device depicted in FIG. 7 can be operated with fluid media flowing continuously into and out of each embryo growth tank 114. Alternatively, fluid media can be periodically urged into and out of each embryo growth tank 114, as desired.

Although not shown in FIG. 7, it will be understood that fluid media valves may also, or alternatively, be provided on each of the growth tank fluid inlet lines 167 which provide fluid communication between main cartridge fluid line 159 and fluid inlet 120 of each embryo growth tank 114. Various types of valves may be employed in cartridge 112, such as microvalves made from a shape-memory alloy ("SMA"), such as Nitinol. These valves can be manufactured very small, and can be easily controlled by the amount of current delivered to the valve. Thus, such valves are suitable for use in cartridge 112, since they allow a control system (as further described herein) to precisely regulate the operation of each valve.

Figure 8:
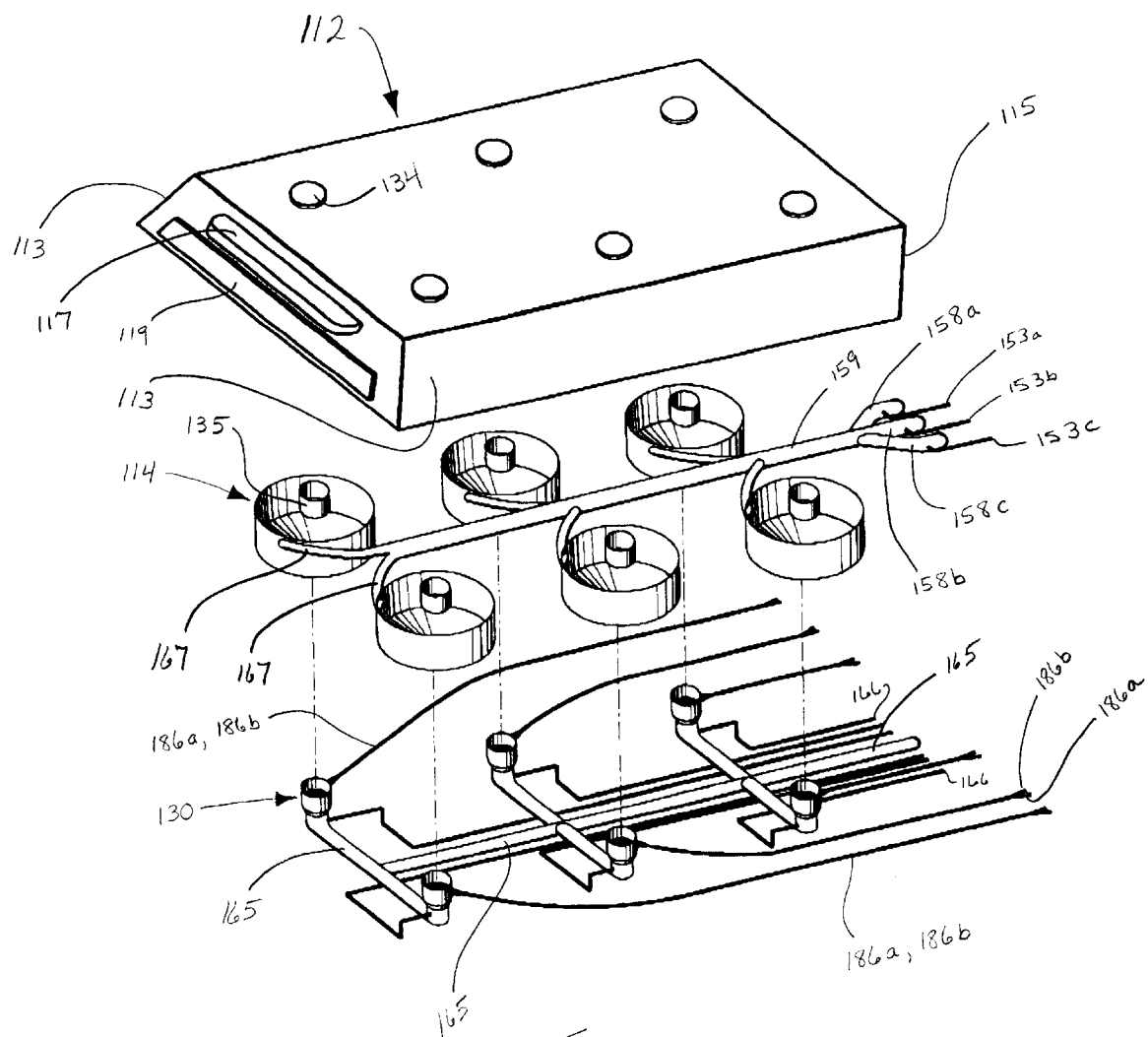
FIG. 8 is an exploded, schematic illustration of a cartridge for use in the IVFT device of FIG. 7.

FIG. 8 is an exploded view of a more specific embodiment of a cartridge 112 according to the present invention. It should be pointed out, however, that FIG. 8 is merely a schematic representation, since cartridge 112 is preferably fabricated as a unitary structure (as best seen in the cross-sectional view of FIG. 9). Cartridge 112 may be manufactured from a variety of materials, such as a non-embryotoxic polymer. Preferably, cartridge 112 is made from a clear, non-embryotoxic plastic, such as ABS or polycarbonate, thereby allowing each embryo to be visually observed. In order to simplify fabrication, cartridge 112 may be formed as a plurality of individual layers which are thereafter secured to one another such as by means of an adhesive. Cartridge 112 may also be configured such that each individual growth tank 114 may be removed from cartridge 112. For example, once one or more of the embryos has reached a stage suitable for placement into the mother, it will often not be necessary to place all of the viable embryos into the mother. Thus, those growth tanks 114 housing embryos which are not to be placed into the mother may be removed from cartridge 112, and the embryos frozen therein (i.e., cryopreserved) for later use. Alternatively, once a portion of the embryos have been removed from cartridge 112 for purposes of implantation, the entire cartridge (including the embryos which are not to be placed into the mother) may be frozen for later use. Prior to freezing tanks 114 or the entire cartridge 112, the fluid media in tanks 114 may be replaced with a suitable cryopreservation media.

Figure 9:
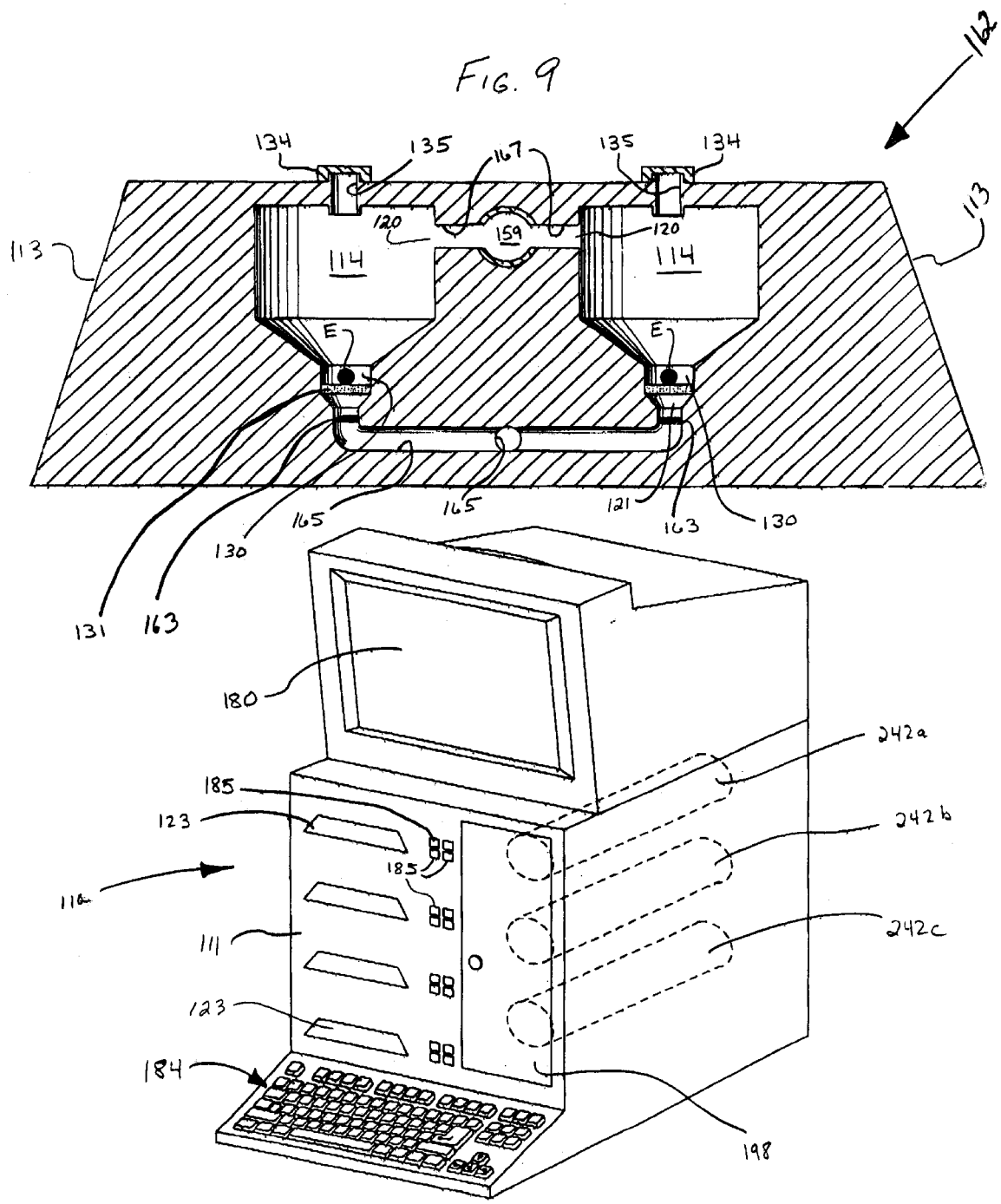
FIG. 9 is a cross-sectional view of a cartridge which may be used in an IVFT device according to the present invention.

As shown in FIGS. 8 and 9, one embodiment of cartridge 112 may generally have a trapezoidal cross-sectional shape. Thus, side walls 113 of cartridge 112 slope downwardly away from the upper surface of the cartridge. As further described herein, this shape helps to ensure that the cartridge is properly inserted into a main system housing. As best seen in FIG. 8, the front wall of cartridge 112 may include a handle 117 which facilitates the insertion and removal of cartridge 112 from the main system housing. The front wall of cartridge 112 also may include a name plate 119, or other written indicia, which identifies the embryos contained within cartridge 1112 (such as by identifying the mother of the embryos contained therein).

Each embryo growth tank 114 may be configured in a variety of shapes, such as the cylindrical configuration shown in FIGS. 8 and 9. As best seen in the cross-sectional view of FIG. 9, wherein the visualization system and electrical connections have been omitted for purposes of clarity, the lower portion of each embryo growth tank 114 may have a frusto-conical shape such that the diameter of embryo growth tank 114 tapers toward embryo well 130. In this manner, gravitational forces, as well as the flow of fluid within embryo growth tank 114, will help to ensure that the growing embryo E will be located within embryo well 130.

As also best seen in FIG. 9, embryo well 130 of growth tank 114 may have a generally cylindrical shape, and may be located at the lower portion of embryo growth tank 114 (adjacent the frusto-conical portion). One wall of well 130, preferably the base of embryo well 130, may comprise a porous layer 131. Porous base 131 may comprise, for example, a microporous filter material. An embryo E will generally be located atop porous base 131, such that base 131 will prevent embryo E from escaping from embryo well 130, while still allowing fluid to pass through porous base 131.

Figure 10:
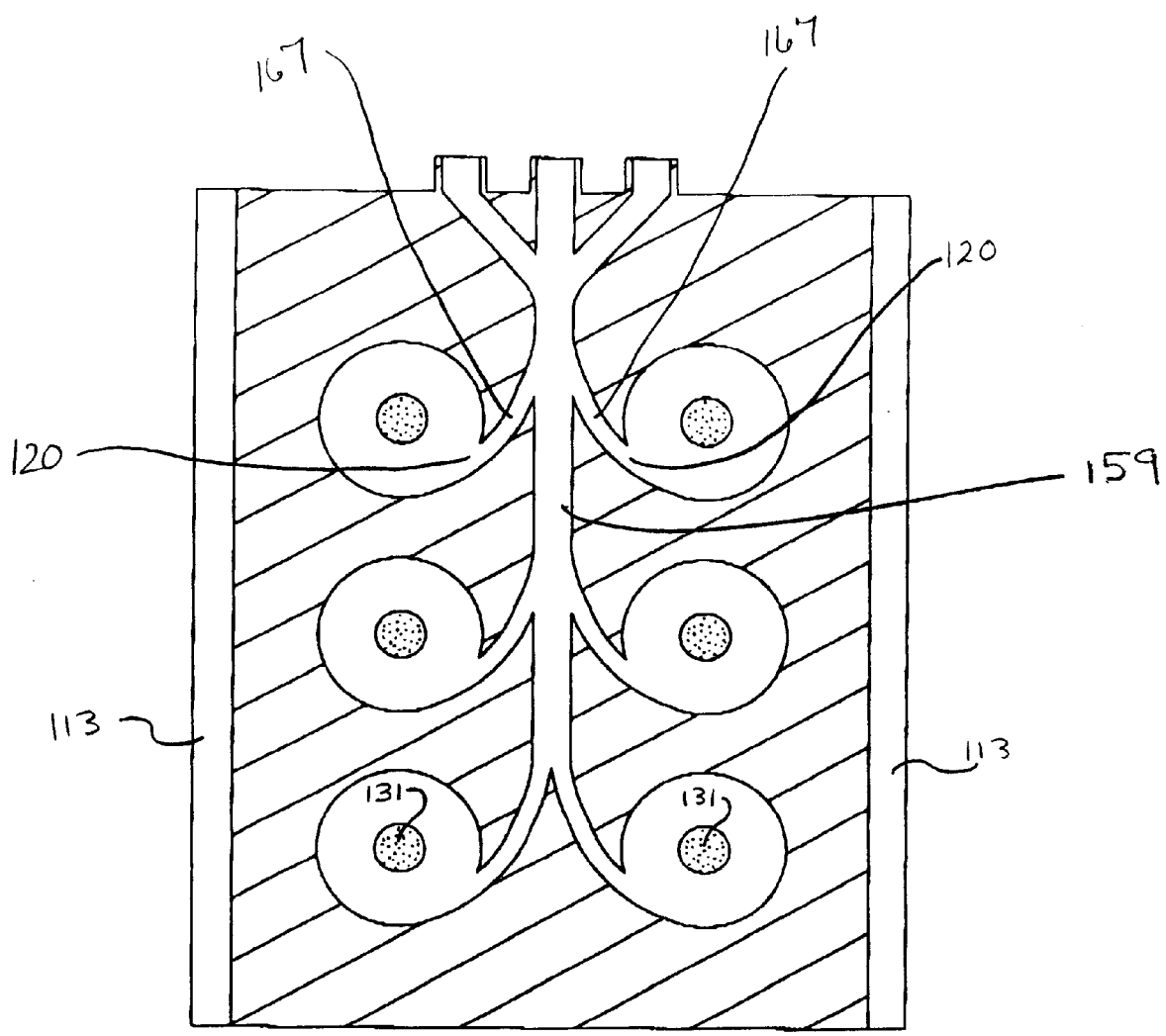
FIG. 10 is a top, cross-sectional view of the cartridge shown in FIG. 8, wherein certain features of the cartridge have been omitted for purposes of clarity.

Growth tank fluid inlet lines 167 provide fluid communication between main cartridge fluid line 159 and fluid inlet 120 of each embryo growth tank 114. Inlet lines 167 may have a variety of configurations, such as extending away from main cartridge fluid line 159 at a 90° angle, and radially inwardly into embryo growth tank 114 (see FIGS. 7 and 9). Alternatively, as shown in FIGS. 8 and 10, embryo growth tank inlet lines 167 may extend curvilinearly away from main fluid line 159, and tangentially into embryo growth tank 114. In this manner, fluid urged into embryo growth tank 114 will flow in a somewhat circular manner within growth tank 114, thereby providing better mixing, as well as a vortex which helps to urge embryo E into well 130.

Each embryo growth tank 114 further includes a fluid outlet 121 adjacent porous base 131 (as best seen in FIG. 9). Thus, when additional fluid is urged into embryo growth tank 114 through fluid inlet 120, waste fluid will be urged out of embryo growth tank 114 through fluid outlet 121. In this manner, fluid will flow across embryo E, thereby helping to remove waste byproducts and cellular debris from well 130 and embryo E. Fluid may even be continuously pumped into each embryo growth tank 114, such that each growing embryo is continuously flushed with new fluid media. Of course it is also contemplated that fluid may be intermittently pumped, or even pulsed, into each embryo growth tank 114, in order to accomplish a similar cleansing effect on the embryo. In fact, pulsing of fluid media into, or even within, tank 114 will cause the embryo to move back and forth, similar to what occurs in the natural fallopian tube.

Fluid media may also be recirculated within cartridge 112 in order to flush cellular debris away from each embryo, as well as to flush embryo waste byproducts away from the embryo, without adding new fluid media to cartridge 112. In order to accomplish such recirculation, a recirculation line may be provided between cartridge discharge line 165 and main cartridge fluid line 159 within cartridge 112. A pump or other suitable circulator may also be provided along this recirculation line in order to provide the desired recirculating fluid flow. In this manner, the build-up of cellular debris and waste byproducts in the fluid surrounding each embryo may be dispersed throughout cartridge 112. One or more recirculation valves may also be provided on the recirculation line within cartridge 112. Alternatively, fluid recirculation may occur outside of cartridge 112, such as by providing a recirculation line which provides fluid communication between waste discharge line 164 and one or more of media inlet lines 148. Once again a recirculation pump and one or more recirculation valves may be provided along such a recirculation line located outside of cartridge 112.

Fluid outlets 121 on embryo growth tanks 114 are in fluid communication with cartridge discharge line 165, such that the fluid urged out of each embryo growth tank 114 will be directed towards waste media outlet port 118 provided on cartridge 112. As shown in the embodiment of FIG. 9, fluid discharge valves 163 may be provided immediately adjacent fluid outlets 121, in order to regulate the discharge of fluid from embryo growth tanks 114.

Each embryo growth tank 114 may also include an embryo port 135 located at the upper end of growth tank 114. Embryo port 135 provides communication between the interior of growth tank 114 and the ambient through the upper surface of cartridge 112. Embryo port 135 may therefore be used to insert a fertilized egg (or an unfertilized egg and sperm) into growth tank 114, as well as to remove an embryo from growth tank 114 for implantation. Preferably, each embryo port 135 is sealed in order to provide a closed environment for growth of the embryo. A cap 134 may be provided for this purpose, and may be attached to port 135 by a variety of means, such as threads, or even an adhesive. Cap 134 may also be made from a polymeric material such as Silastic, so that a fertilized egg or embryo may be inserted into and removed from growth tank 114 using a simple syringe which penetrates cap 134 (which acts as a septum). The needle of the syringe will readily penetrate polymeric cap 134, thereby allowing the fertilized egg or embryo to be inserted into, or removed from growth tank 114. When the needle is removed from cap 134, the cap will then self-seal, thereby maintaining a closed environment within embryo growth tank 114.

In order to provide a suitable environment for growing embryos, the IVFT device of FIG. 7 may also include a heater 154. A variety of devices may be used for heater 154, such as a simple air heater which emits warm air throughout the device. In addition, one or more of the fluid media reservoirs 142 may include a heater 147 for heating the fluid media housed within the media reservoir. In this manner, not only will cartridge 112 be maintained at the proper temperature by heater 154, fluid media pumped into cartridge 112 may also be maintained at or near that same temperature such that the embryo will not experience large temperature fluctuations even when new fluid media is pumped into cartridge 112.

The IVFT device of FIG. 7 also preferably includes a control system for regulating the environment in which the embryos are grown. Unlike prior art embryo growth methods wherein the embryo is transferred from one petri dish of fluid media to another, the IVFT device depicted in FIG. 7 allows each embryo to remain undisturbed within its embryo growth tank 114 throughout the period of in vitro growth. The fluid media within each embryo growth tank may be changed, as needed, without manipulating the embryo. In addition, the fluid pressure, temperature and other conditions within growth tank 114 may be adjusted as desired. The control system of the IVFT device of FIG. 7 further allows the conditions within embryo growth tank 114 to be monitored and adjusted in accordance with a predetermined schedule and/or in response to sensed conditions of the embryo (such as its growth) and/or conditions within the embryo growth tank.

Figure 11:
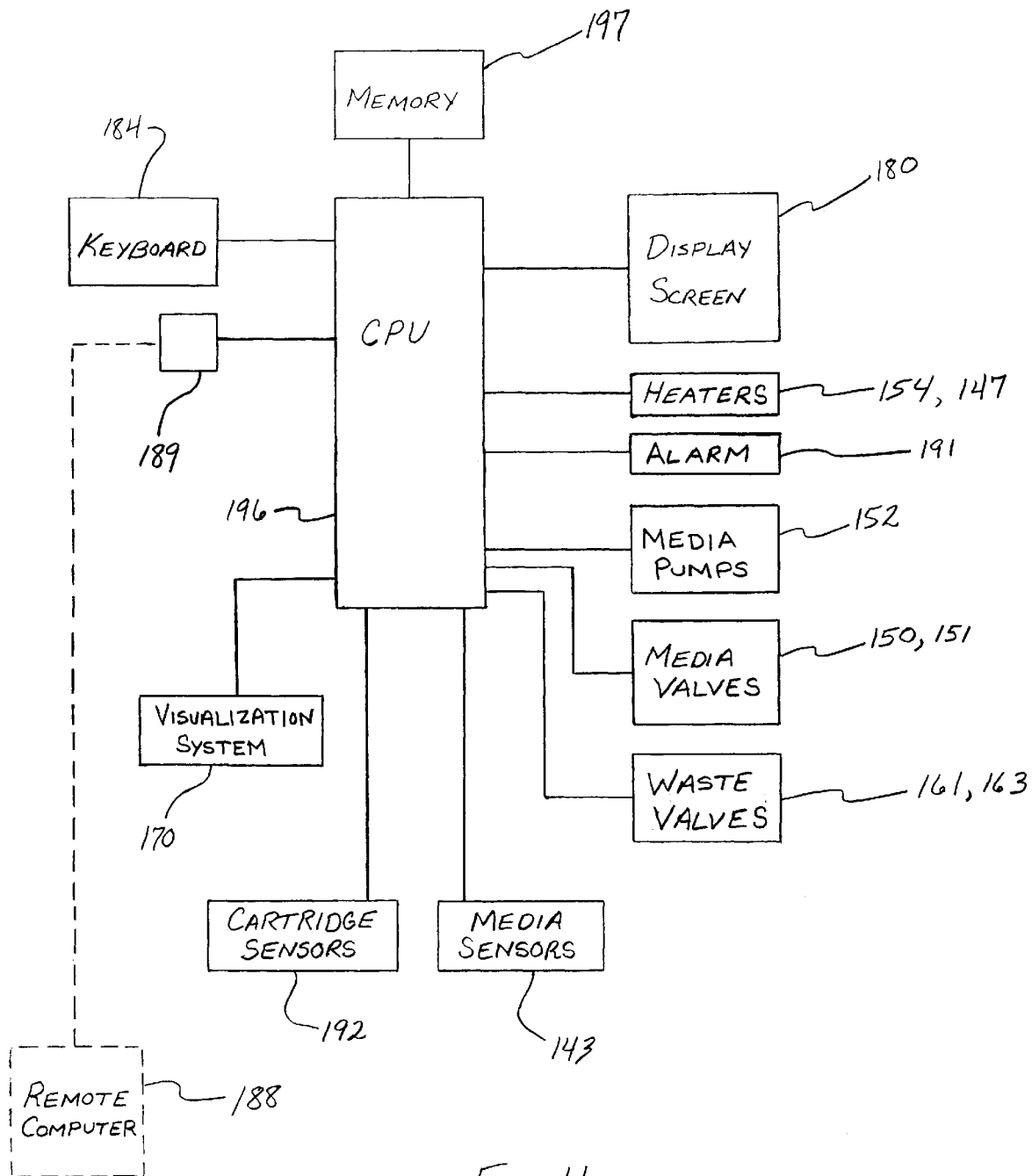
FIG. 11 is a schematic illustration of a control system which may be used with an IVFT device according to the present invention.

FIG. 11 is a schematic representation of a control system which may be employed with the IVFT device of FIG. 7. A processor, such as CPU 196, is configured for monitoring, analyzing, and/or controlling embryo growth conditions. CPU 196 operates in accordance with instructions stored in memory 197 (preferably including both RAM and ROM), as well as instructions provided by the user through a keyboard 184, a remote computer 188 or other input device well-known to those skilled in the art. Data may also be displayed to the user on a display screen 180.

One or more cartridge sensors 192 may provide data indicative of conditions within cartridge 112 to CPU 196, particularly conditions within each of the embryo growth tanks 114. Similarly, one or more media sensors 143 may provide data indicative of conditions within fluid media reservoirs 142 to CPU 196. In response to data received from sensors 192 and 143, CPU 196 controls the operation of media pumps 152, media valves 150 and 151, waste valves 161 and 163, heaters 154 and 147, and one or more alarms 191. In addition, a visualization system 170 (further described below) may also provide data to CPU 196 for processing, as well as for display on display screen 180. Although a preferred embodiment of the IVFT device depicted in FIGS. 7 and 11 includes a keyboard 184 for controlling and monitoring the operation of the device, a remote computer 188 may also be used for the same purpose. Thus, a suitable interface 189 (such as a modem, network interface card, USB port, or other device well-known to those skilled in the art) is provided in order to allow a remote user to access the device by means of a remote computer 188. For example, a doctor monitoring the growth of embryos in the IVFT device may access the device using a personal computer and a modem.

A variety of media sensors 143 may be provided, such as a temperature sensor 143a and a fluid level sensor 143b (see FIG. 7). Temperature sensor 143a and fluid level sensor 143b may be positioned within one or more of the media reservoirs 142, and are in electrical communication with CPU 196. A suitable temperature sensor 143a may comprise, for example, a thermistor which is in electrical communication with CPU 196 through an A/D convertor. In this manner, temperature sensor 143a will provide data to CPU 196 indicative of the temperature of fluid within media reservoir 142a. A temperature set point may be stored in memory 197 and provided to CPU 196, or the user may input a fluid media temperature set point by means of keyboard 184. If the temperature of fluid within media reservoir 142a falls below the set point (as measured by temperature sensor 143a), CPU 196 will send a signal activating or increasing the output of heater 147 in order to increase the temperature of fluid within media reservoir 142a.

A fluid level sensor 143b may be used to provide data indicative of the fluid level within media reservoir 142a to CPU 196. If the fluid level falls below a predetermined set point, CPU 196 may activate an alarm 191 in order to signal the user that additional fluid is needed in reservoir 142a. Alarm 191 may comprise any of a variety of audible or visual alarms, such as a flashing light and/or an audible sound. It should also be pointed out that multiple alarms 191 may be provided in the IVFT device, such that each alarm 191 is configured to indicate a different problem or condition to the user. Alarm 191 may even compromise a remote notification system which alerts a doctor or other individual who is remote from the IVFT device (such as by means of a pager, cellular phone, or similar device) that the fluid level is low, or that another problem or condition exists within the IVFT device. Various other media sensors 143 may also be provided either within fluid reservoirs 142, and/or within fluid media inlet lines 148, thereby providing additional data to CPU 196. Other exemplary sensors include, for example, fluid flow meters (for indicating the amount of fluid urged into cartridge 112), pH sensors, oxygen sensors, carbon dioxide sensors, osmolarity sensors (for measuring the osmotic pressure of a fluid), or any other sensor which provides useful data concerning the fluid media.

By way of further example, an oxygen sensor may be provided in one or more of fluid reservoirs 142, with each sensor in electrical communication with CPU 196 in order to provide CPU 196 with an electrical signal indicative of the level of dissolved oxygen in the fluid contained within reservoirs 142. Many fluid medias used for growing embryos are provided with a certain level of oxygen dissolved therein. Monitoring fluid oxygen levels can provide an indication of when a fluid media in a reservoir 142 has aged or otherwise deteriorated (i.e., by a diminished level of dissolved oxygen). Thus, CPU 196 may activate an alarm or other indicia which indicates to an operator that the fluid media in a reservoir 142 needs to be replaced. Similar sensors (such as a pH sensor, carbon dioxide sensor, or an osmolarity sensor) can be employed to indicate to the user that the fluid media in a reservoir 142 is unsuitable for use and should be replaced.

Various cartridge sensors 192 may be provided within cartridge 112 in order to provide data to CPU 196. Cartridge sensors 192 may be located within each embryo growth tank 114 and/or within one or more of the various fluid lines within cartridge 112. By way of example, a temperature sensor 192a may be provided within main cartridge fluid line 159, in electrical communication with CPU 196. In this manner, data indicative of the temperature within cartridge 112 may be provided to CPU 196, so that CPU 196 may control the operation of heater 154 (and optionally heater 147) in order to regulate the temperature within cartridge 112.

Similarly, a pressure sensor 192b may also be provided within main cartridge fluid line 159 in order to monitor the fluid pressure within cartridge 112. Pressure sensor 192b is also in electrical communication with CPU 196, such that a signal from pressure sensor 192b may be used to monitor and control the fluid pressure within cartridge 112. For example, CPU 196, in response to data received from pressure sensor 192b, may regulate the operation of one or more of pumps 152, and/or one or more of fluid media valves 150, 151, 161, and 163, in order to regulate the fluid pressure within cartridge 112. It should be noted that cartridge sensors 192 (such as temperature sensor 192a and pressure sensor 192b) may also, or alternatively, be provided within each embryo growth tank 114 in order to individually monitor the conditions within each growth tank 114. For example, an urea sensor 192c may be provided in one or more of tanks 114, in electrical communication with CPU 196. A variety of other sensors may also be provided in cartridge 112 (including within each tank 114), such as osmolarity sensors, as well as one or more sensors for detecting levels of $O_2$, $CO_2$, ammonia, and/or $N_2$.

Sensors for detecting levels of urea, $CO_2$, ammonia, $N_2$, or other embryo waste products or materials which may otherwise be harmful to the embryo may be particularly useful in providing an indication that the fluid within cartridge 112 or an individual tank 114 needs to be changed or otherwise circulated to remove such materials away from the embryo (such to a waste reservoir). For example, CPU 196 may determine that, on the basis of signals from one or more such sensors and comparing those signals to one or more predetermined set points, elevated waste levels are present in a cartridge. When this occurs, CPU 196 may activate the fluid supply system in order to pump new fluid media into the cartridge and urge the old, waste-contaminated fluid media out of the cartridge. In addition, this process will also help to flush debris and waste materials away from the embryos and into the waste reservoir. In this manner, the device will ensure that the embryos do not remain in a potentially toxic environment for an extended period of time. Of course it is also contemplated that new fluid media may be urged into each cartridge according to a predetermined schedule, and/or in response to embryo growth, thereby also helping to remove potentially toxic waste away from each embryo.

It will also be understood that one or more sampling ports may be provided, such as on discharge line 164, thereby allowing a sample of waste fluid media to be drawn and analyzed (such as by using conventional test methods for oxygen, carbon dioxide, urea, nitrogen, ammonia, and other waste byproducts). The test data may then be input into the IVFT device, using, for example, keyboard 184 (or other input device). Sampling ports may similarly be provided at a variety of other locations in the system, such as described previously.

As with the previously-described embodiments, the IVFT system shown in FIG. 11 may include a visualization system or assembly 170 which allows embryo development to be observed without the need for physically manipulating the embryo. While the visualization assembly described previously can be employed in the embodiment of FIG. 11, an alternative visualization 170 utilizes fiber optics for embryo visualization.

Figure 12:
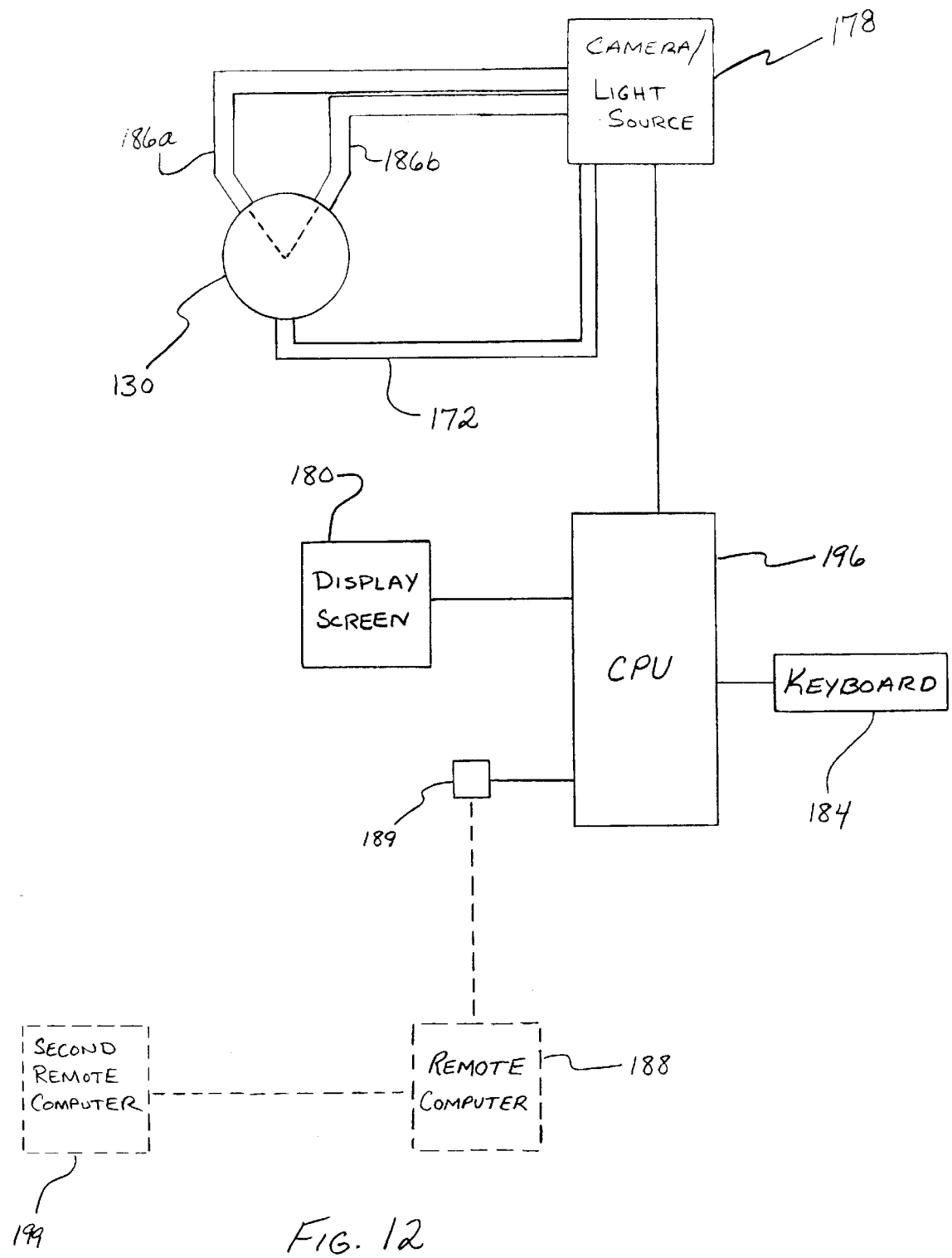
FIG. 12 is a schematic illustration of a visualization system which may be used with an IVFT device according to the present invention.
Figure 13:
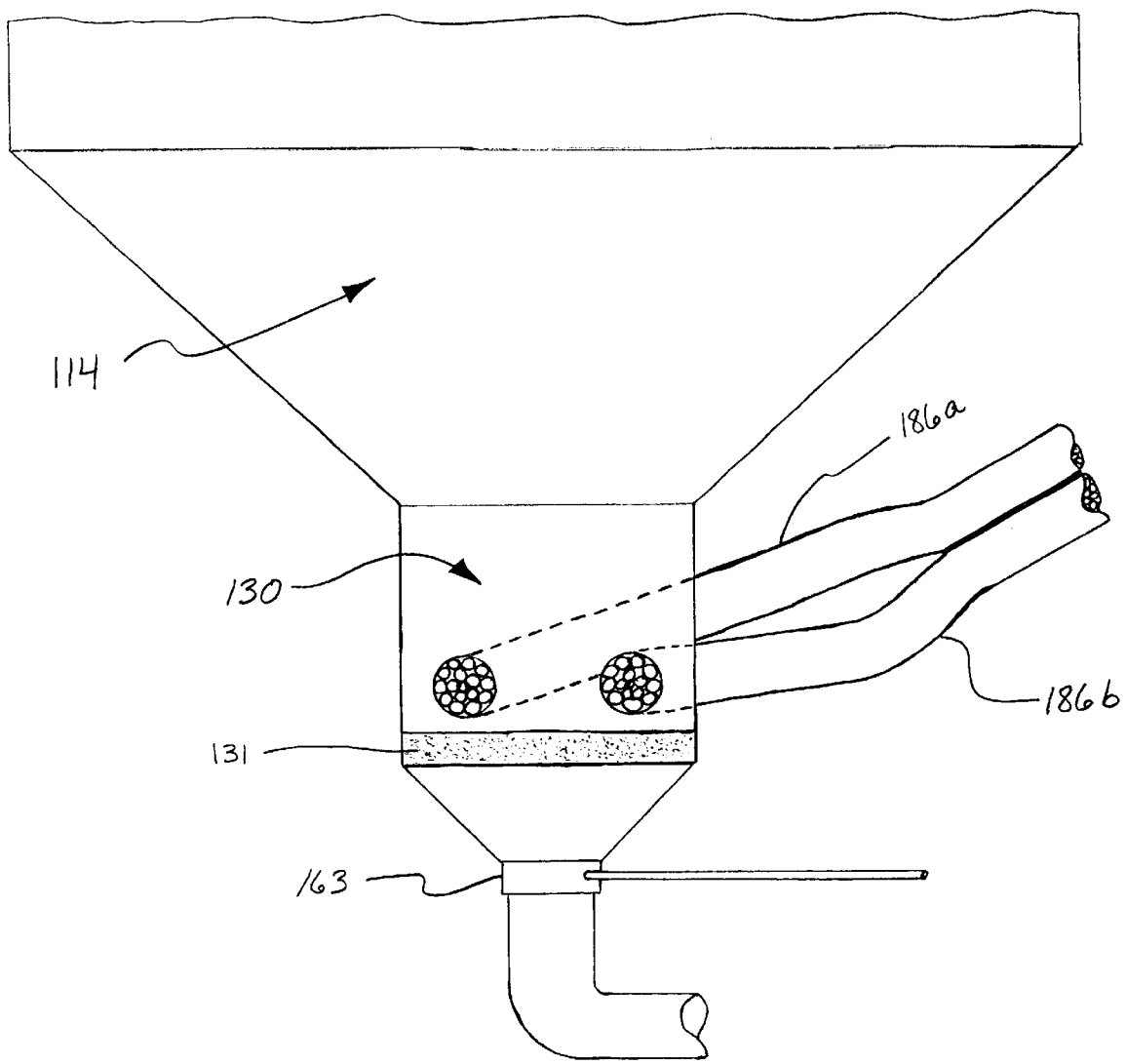
FIG. 13 is a schematic illustration of a portion of an embryo growth tank according to one embodiment of the present invention.

FIG. 12 is a schematic illustration of an exemplary visualization system according to one embodiment of the present invention. In the embodiment of FIG. 12, at least one fiber optic bundle 186a, and preferably two fiber optic bundles 186a and 186b, are in light transmitting communication with embryo well 130. As best seen in FIG. 13, fiber optic bundles 186a and 186b may terminate near the base of embryo well 130, and are positioned such that light may be transmitted between the interior of embryo well 130 and fiber optic bundles 186a and 186b. Preferably, fiber optic bundles 186a and 186b are spaced apart from one another in the region adjacent embryo well 130 in order to provide stereoscopic visualization of a growing embryo within embryo well 130 (as further described below). The exterior walls of embryo well 130 are preferably transparent in order to allow light to pass therethrough. In addition, a lens may be provided at the end of each fiber optic bundle 186, and such lens may even comprise a portion of the exterior wall of embryo well 130 itself. In this manner, the lenses will help focus light exiting from, or entering into, fiber optic bundles 186a and 186b.

Fiber optic bundles 186a and 186b are also in light transmitting communication with a camera 178, which may also double as a light source. Alternatively, separate camera and light source assemblies may be utilized. Camera 178 may comprise any of a variety of structures well-known to those skilled in the art, particularly those cameras typically used with fiber optic endoscopes (such as a CCD camera). In this manner, an image of a growing embryo housed within embryo well 130 will be transmitted along fiber optic bundles 186a and 186b to camera 178. While camera/light source assembly 178 may include its own screen, eyepiece, or other device for viewing an image of the interior of embryo well 130, camera/light source 178 is preferably in electrical communication with CPU 196. In this manner, a digital image of the interior of embryo well 130 (and a growing embryo therein) will be provided to CPU 196 for further processing and display on display screen 180. These images can also be stored for later retrieval and viewing, including viewing by means of remote computer 188. Since cartridge 112 is preferably made from a transparent plastic, the embryos therein may also be viewed by conventional means, such as by placing the entire cartridge (or even a singe, removable tank 114) under a microscope.

In order to obtain a suitable image of the interior of embryo well 130, it will generally be necessary to provide illumination light within embryo well 130. While a simple lamp may be used to eliminate the entire cartridge 112, each embryo well 130 may also be illuminated individually, and only when needed for visualization purposes. By way of example, a third fiber optic bundle 172 may also be provided such that light from fiber optic bundle 172 is directed into embryo well 130 (as shown in FIG. 12). Third fiber optic bundle 172 is in light transmitting communication with a light source, such as camera/light source 178. In this manner, light from camera/light source 178 is directed along fiber optic bundle 172, and into embryo well 130 in order to illuminate the interior of embryo well 130 (including an embryo housed therein). In this manner, illumination light will be provided such that a more suitable image can be obtained through fiber optic bundles 186a and 186b.

Alternatively, fiber optic bundles 186a and 186b may be employed for illuminating the interior of embryo well 130. Since each fiber optic bundle 186a and 186b preferably comprises a plurality of individual fiber optic filaments, a portion of those filaments can be used for transmitting light from camera/light source 178 into the interior of embryo well 130. The remaining portion of the fiber optic elements of bundles 186a and 186b can then be used to transmit an image of the interior of embryo well 130, as described previously.

In the embodiments employing dual fiber optic bundles 186a and 186b for visualization purposes, a stereoscopic image may be provided. Thus, fiber optic bundles 186a and 186b, as well as any lens elements employed therewith, should be positioned for acquiring a stereoscopic image of the interior of embryo well 130. In this manner, a stereoscopic image of a growing embryo may be provided on display screen 180, thereby allowing the user to more accurately monitor the development of the growing embryo.

By way of example, the user may employ the stereoscopic image in order to visually count the number of cells in the embryo at any given time. Since the cell count of an embryo, particularly when plotted against time, provides an indicator of embryo growth and viability, cell counts may even be used to adjust the environment within embryo well 130 (such as changing fluid media, altering the temperature, or adjusting the fluid pressure therein). For example, a user may periodically view a growing embryo on display screen 180 in order to count the number of cells in the embryo. Thereafter, the user will input the cell count via keyboard 184. CPU 196, in accordance with instructions stored in memory 197, will then utilize the cell count data in order to determine the growth status of the embryo. If the embryo has reached a certain developmental stage (i.e., a certain number of cells), CPU 196 may then alter the conditions within embryo well 130. In this manner, conditions within embryo well 130 are altered based on the development of the individual embryo therein, rather than a predetermined schedule established on the basis of typical embryo growth. For example, once the embryo has reached a certain number of cells (e.g., eight), CPU 196 may send signals to the various pumps and valves within the system such that a second fluid media is delivered to the embryo, rather than the first fluid media in which the embryo had been growing up until that time. In addition, the cell counting process may also be performed by CPU 196 in accordance with software instructions provided by memory 197, rather than a visual count performed by a user.

It should be pointed out that fiber optic bundles 186a and 186b are preferably provided for each individual embryo well 130 of cartridge 112 (see FIG. 8). Each of the fiber optic bundles may be in light transmitting communication with camera/light source 178 such that individual images of each embryo well 130 may be obtained. While separate cameras and light sources may be provided for each fiber optic bundle, camera/light source 178 may alternatively include a routing system which allows a single camera and a single light source to be employed. The routing system is configured such that only one set of fiber optic bundles 186a and 186b will be in light transmitting communication with the camera portion of camera/light source 178. Although such an arrangement only allows the visualization of a single embryo well 130 at any given time, it will reduce the cost of having multiple cameras within the IVFT device. In addition, a continuous image of a growing embryo is generally not needed, since periodic visualization of the embryo will suffice. CPU 196 may also be configured such that it instructs camera/light source 178 to acquire an image of each embryo within cartridge 112 at predetermined intervals. These images may then be stored in memory 197 for later retrieval, analysis and/or display on display screen 180.

While cell counts provide a suitable method of monitoring the nuclear mass (and hence growth) of the embryo, optical density measurements may also be employed for monitoring the nuclear mass of the embryo. Thus, camera/light source 178 or CPU 196 may be configured to measure the amount of light transmitted through an embryo. For example, third fiber optic bundle 172 may direct light towards a growing embryo within embryo well 130 from a side opposite to the location of fiber optic bundles 186a and 186b. Camera/light source 178 will direct a predetermined quantity of light through third fiber optic bundle 172 into embryo well 130. Since light from third fiber optic bundle 172 which is transmitted through the embryo will be acquired by fiber optic bundles 186a and 186b, the intensity of such light may be measured by camera/light source 178 or CPU 196. In this manner, the light transmissive properties (i.e., the optical density) of the growing embryo can be readily determined by CPU 196 in accordance with instructions stored in memory 197.

Since the optical density of an embryo increases as the nuclear mass (i.e., number of cells) of the embryo increases, the optical density can be used to indirectly determine the number of cells in the embryo. A look-up table may be stored in memory 197 by which the optical density can be correlated to the number of cells in the embryo. The look-up table can be populated, for example, by previously-acquired test data correlating the optical density to the number of cells in an embryo. In this manner, the number of cells in the growing embryo can be readily determined by CPU 196, without requiring a user to visually count the number of cells, or otherwise manipulate the embryo. Of course, optical density measurements can be used as a direct measurement of embryo growth (i.e., without a conversion to cell count via a lookup table), such as by plotting optical density (of the log of optical density) vs. time. This plot (or the rate of growth as measured by the optical density) may be compared to typical, predetermined data in order to determine whether or not the embryo is growing at a normal or optimal rate (i.e., not too fast, and not too slow). An alarm for indicating an abnormal growth rate may even be provided.

As described previously, the IVFT system shown in FIG. 12 can be configured such that an image of each embryo within a cartridge 112 is acquired at predetermined intervals. These images can then be processed, such as by CPU 196, and stored in memory (such as memory 197). Each image may then be recalled by the user, such as by inputting instructions on keyboard 184, so that the image is displayed to the user on display screen 180. A series of images of a single embryo may even be displayed sequentially on display screen 180, such that a "time-lapse" image sequence is provided. In addition, a remote user may even access the system through a remote computer 188 and a suitable interface 189, such that the remote user can also view the embryo images stored within memory 197.

As yet another alternative, the embryo images may be uploaded to a remote computer 188, such that a second remote computer 199 may access the embryo images on first remote computer 188. For example, parents may utilize a direct modem connection, or even an Internet connection, to access remote computer 188 by means of a second remote computer 199 (such as a PC). With such an arrangement, the parents may safely view the embryo images without directly accessing CPU 196 or other components of the IVFT device.

Figure 14:
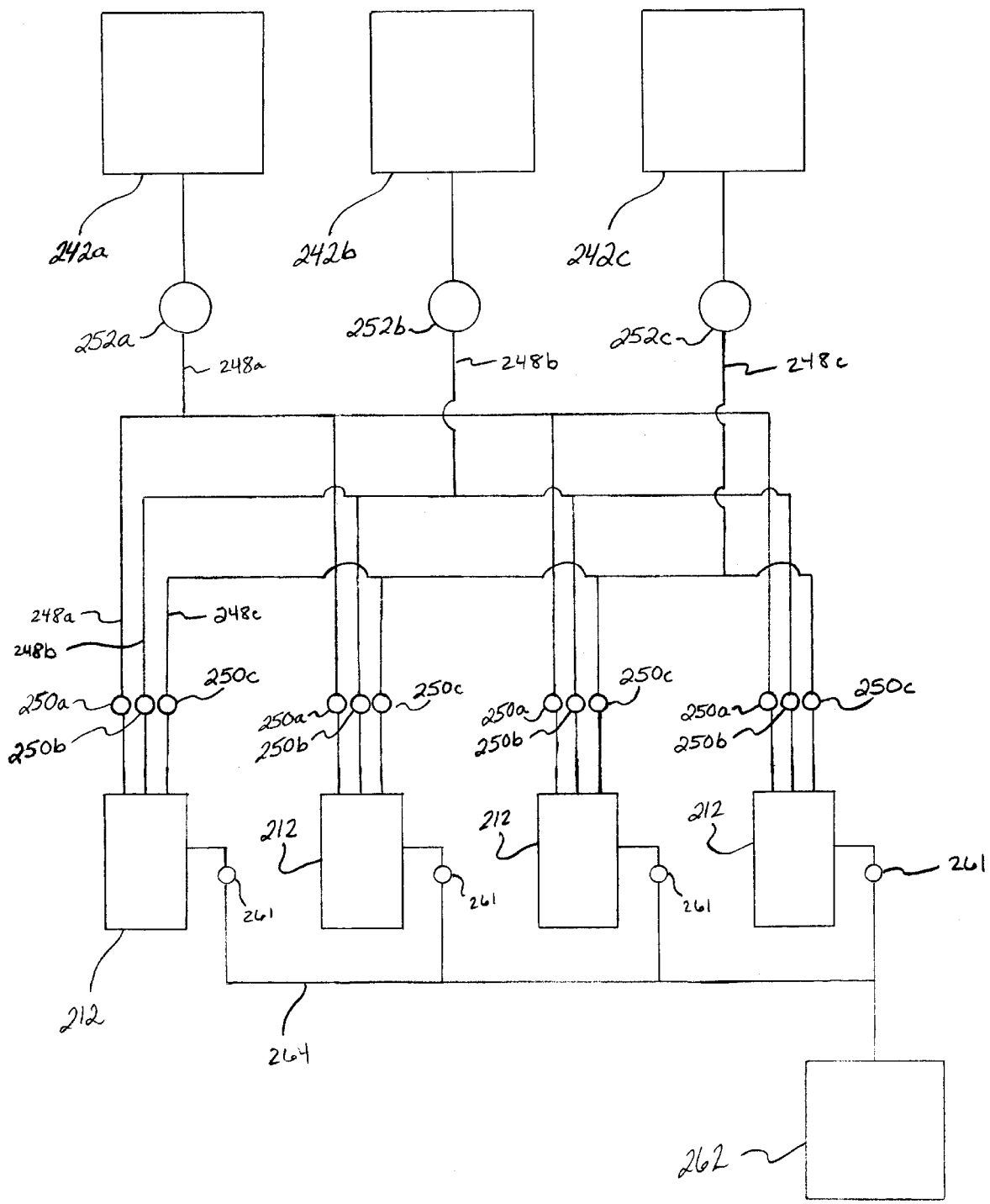
FIG. 14 is a schematic flow diagram of yet another embodiment of an IVFT device according to the present invention.

While the embodiment shown in FIG. 7 depicts a single cartridge 112 for growing embryos therein, an IVFT device according to the present invention may be configured such that multiple cartridges are employed. FIG. 14 schematically depicts such an IVFT device, wherein four cartridges 212 are provided. It will be understood, however, that the IVFT device may include any number of cartridges, and that shown in FIG. 14 is merely exemplary of one possible embodiment.

Although the embodiment of FIG. 14 employs four cartridges 212 for growing embryos therein, it is not necessary to provide separate fluid media tanks for each cartridge. Therefore, first, second and third fluid media reservoirs 242a, 242b and 242c are provided, wherein each reservoir may be selectively placed in fluid communication with one or more of cartridges 212. Fluid media pumps 252a, 252b and 252c may be provided on each of the fluid media inlet lines 248a, 248b and 248c. Each fluid media inlet line 248 may then branch into multiple lines, each feeding into one of the cartridges 212. In other words, fluid media inlet line 248a provides fluid communication between first fluid media reservoir 242a and each of the four cartridges 212. Separate fluid media valves 250a, 250b and 250c may also be provided along each of the fluid media inlet lines, preferably after each fluid media line has branched into separate inlet lines for each of the cartridges 212. Thus, as shown in FIG. 14, twelve such fluid media valves 250 are provided, three for each cartridge. An individual waste valve 261 may be provided for each cartridge 212 in order to regulate the flow of waste fluid out of each cartridge. A discharge line 264 provides fluid communication between waste reservoir 262 and each of the four cartridges 212, as shown.

It should be pointed out that in the IVFT device shown in FIG. 14, each cartridge 212 may be configured similarly to the various embodiments of cartridge 112 described previously. Thus, additional valves and fluid lines may be provided within each cartridge 212, in the manner described previously. Separate sensors are also preferably provided within each cartridge 212, thus allowing the individual conditions within each cartridge 212 (and even each growth tank) to be individually monitored, analyzed and adjusted as needed.

FIG. 15 is a perspective view of one embodiment of an IVFT device according to the present invention, wherein the device is configured to accommodate up to four separate cartridges for growing one or more embryos therein. The IVFT device of FIG. 15 includes a main system housing 110 having an incubator portion 111, a display screen 180 and a keyboard 184. Incubator portion 111 is configured for housing fluid media reservoirs 242a, 242b and 242c, individual cartridges 212 placed therein, fluid waste reservoir 262, the various fluid lines described previously, as well as the various pumps and valves described previously, and heater 154. The control system elements of the IVFT device (such as CPU 196 and memory 197, for example) may be housed within incubator portion 111, or even adjacent display screen 180 (so that heat from heater 154 will not adversely affect the electronic components of the IVFT device.

It should also be noted that a CPU 196, memory 197, and other components of the control system may even be provided within each cartridge 112, thus providing a "smart" cartridge which includes its own control system. Alternatively, CPU 196, memory 197, and other elements of the control system may be provided by an external computer (such as a PC, particularly a laptop PC) which is operatively connected to main system housing 110 (such as by means of a suitable interface, such as an USB port or other well-known interface for connecting a laptop PC to another device). In this manner, CPU 196, for example, will comprise the processor of the laptop computer. It will also be understood that the term "CPU" is intended to encompass any of a variety of well-known processors, including general purpose processors. In addition, devices according to the present invention may also include multiple processors for performing the various functions described herein. It will also be understood that power may be provided by means of an external power cord and/or one or more internal power supplies. A battery backup power supply may also be provided to ensure that the IVFT device will continue to operate properly if the main power source (e.g., a wall outlet) becomes inoperable.

Incubator portion 11 is preferably insulated such that heat provided by heater 154 will be retained therein. An access door 198 may also be provided on incubator portion 111 in order to allow access to the interior thereof. In this manner, additional fluid media may be added to fluid media reservoirs 242. Cartridge openings 123 may also be provided on the front face of incubator portion 111, and should be configured to receive a cartridge 212 therein. Thus, each cartridge opening 123 is depicted as having a trapezoidal shape in order to accommodate the cross-sectional shape of cartridge 212. In this manner, each cartridge 212 can only be inserted in a single orientation. Protective hinged doors or other barrier members may also be provided on cartridge openings 123 in order to assist in maintaining a closed environment within incubator portion 111.

While keyboard 184 may be employed to input information into the IVFT device, as well as to monitor, analyze and control the operation of the device and the growth of embryos therein, additional input devices may also be provided. Thus, for example, one or more input switches 185 may be provided adjacent each cartridge opening 123 for this purpose. Each input switch 185 may comprise, for example, a pressure-sensitive switch which allows the user to activate a function or feature of the IVFT device. For example, by pressing one of the input switches 185 adjacent a particular cartridge opening 123, the user may instruct CPU 196 to display an embryo image from that cartridge on display screen 180. The same switch, or another of input switches 185 adjacent thereto, may then be activated in order to scroll through images of each of the embryos growing within that cartridge. Another of input switches 185 may be activated to display on display screen 180 certain conditions within a cartridge, such as the optical density or cell count of the embryos in that cartridge, or other data of interest (e.g., the temperature or fluid pressure within the cartridge). Of course input switches 185, as well as keyboard 184 may be used to display a variety of other data, as well as to monitor and control the operation of the IVFT device.

Figure 16:
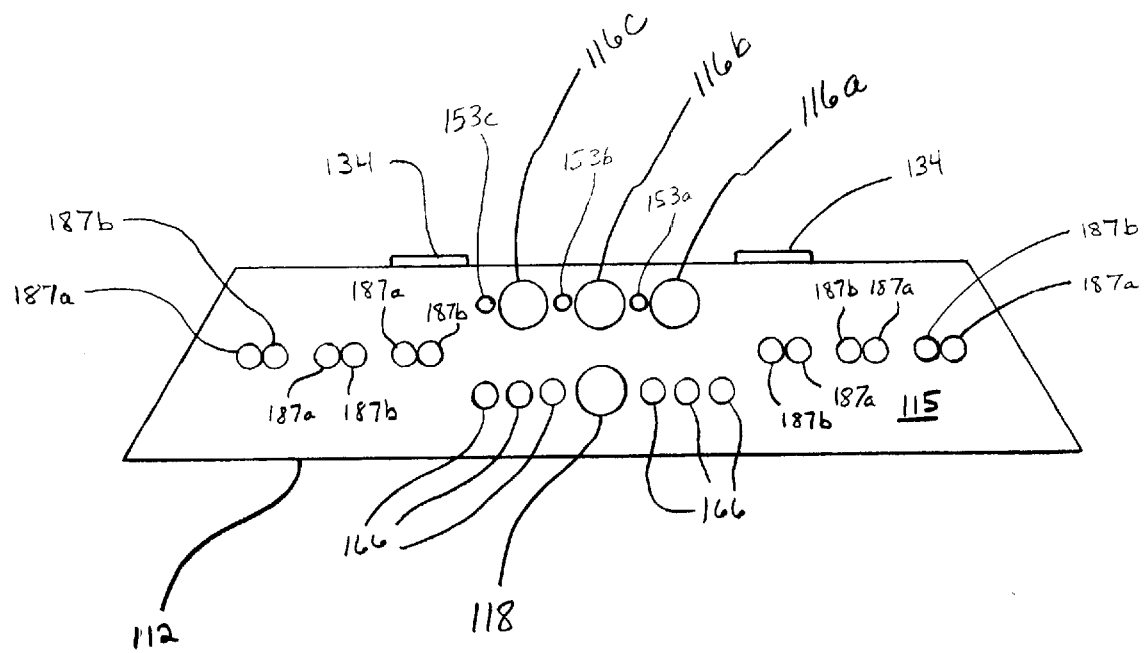
FIG. 16 is an end plan view of a cartridge which may be used in an IVFT device according to the present invention.

When an IVFT device such as that shown in FIG. 15 is employed, it is preferred that each cartridge is configured such that it may be easily inserted and removed from the system housing 110. Preferably, each cartridge may be inserted into main system housing 110 without disturbing any embryos contained within the cartridge, as well as in a manner which prevents leakage of any fluid from the cartridge. FIG. 16 is a plan view of the end wall 115 of a cartridge 112. A variety of connection elements are provided on end wall 115, and are arranged such that each will connect with a corresponding connection element within main system housing 110. Thus, fluid media inlet ports 116a, 116b and 116c are provided on end wall 115, and are arranged such that when cartridge 112 is inserted into main system housing 110 through a cartridge opening 123, fluid media inlet ports 116 will each mate with a suitable connector within main system housing 110 (such as a hollow point connector element, as described previously). Similarly, waste fluid media outlet port 118 is also provided on end wall 115, and is configured to mate with a corresponding connector element within main system housing 110.

A plurality of electrical connectors may also be provided on end wall 115, and these connectors may have any of a variety of configurations well-known to those skilled in the art. For example, male electrical connectors may extend away from end wall 115, and corresponding female connectors may be provided within main system housing 110. Alternatively, female connector elements may be provided on end wall 115 (such as extending into cartridge 112 away from end wall 115), and corresponding male electrical connector elements may be provided within main system housing 110. In the embodiment shown in FIG. 16, electrical connector elements 153a, 153b and 153c are provided on end wall 115, and are in electrical communication with fluid media valves 151a, 151b and 151c in cartridge 112 (see FIGS. 7 and 8). When individual discharge valves 163 are provided for each embryo growth tank 114 (see FIG. 7), electrical connectors 166 for each of the discharge valves 163 may also be provided on end wall 115 of cartridge 112 (as shown in FIG. 16).

When the IVFT system includes a visualization system, end wall 115 of cartridge 112 may include suitable connectors for each of the fiber optic bundles contained within cartridge 112. Thus, in the example of FIG. 16, six pairs of light ports 187a and 187b are provided, wherein each set of light ports is in light transmitting communication with fiber optic bundles 186a and 186b for a particular embryo well 130. Such light ports can comprise any of a variety of structures well-known to those skilled in the art for placing fiber optic bundles in light transmitting communication with other fiber optic bundles. Thus, main system housing 110 includes corresponding light ports which may be in communication with, for example, additional fiber optic bundles which are used to route light to camera/light source 178. When a third fiber optic bundle 172 is employed for each embryo well 130, additional light ports will be provided on end wall 115 and within housing 110 in the same manner.

In order to use the various embodiments of the IVFT device shown in FIGS. 7–16, the user will first select a cartridge 112, preferably one which has not been previously used. Once the sperm and ovum (i.e., egg) have been collected by conventional means, the sperm and ovum may be placed in close proximity to each other such that the ovum is fertilized. After fertilization, the embryo is then transferred into an embryo growth tank 114 of the cartridge. The cartridge may already include fluid media therein, such that the embryo will be deposited into an embryo growth tank 114 containing a suitable fluid media (such as a pH adjusted, amino acid based nutrient media. The embryo may be deposited into embryo growth tank 114 by, for example, injecting the embryo using a syringe inserted through septum 134. The embryo will generally fall into embryo well 130 due to gravitational forces. Additional embryos may be inserted into one or more of the other embryo growth tanks 114. Each cartridge may house embryos from the same mother, or from different mothers, since the embryos are segregated from one another within cartridge 112.

As an alternative to fertilizing the egg outside of cartridge 112, fertilization may even take place within embryo growth tanks 114 in cartridge 112. Thus, an unfertilized egg may be injected into an embryo growth tank 114 in the manner described above. Thereafter, sperm may be injected into that same embryo growth tank 114 such that the sperm and egg will now be in close proximity to one another for purposes of fertilization. When fertilization within cartridge 112 is employed, the pre-loaded fluid in cartridge 112 is preferably of a variety suitable for fertilization purposes (such as a pH adjusted, amino acid based nutrient media). Additional eggs may be inserted into one or more of the other embryo growth tanks, along with sperm for fertilization purposes. When fertilization in cartridge 112 is employed, it is preferable that the cartridge contain eggs from one donor, rather than multiple donors, thereby avoiding any cross-fertilization.

Once the embryos (or sperm and eggs) have been injected into one or more of the embryo growth tanks 114 of a cartridge 112, the cartridge may then be inserted into main system housing 110 through a cartridge opening 123. Preferably, main system housing 110 should be fully operational, with the interior of incubator portion 111 at the desired temperature. The user may then utilize keyboard 184 and/or input switches 185 in order to provide an indication to CPU 196 that a new cartridge has been inserted. Once the cartridge device has been inserted, CPU 196 will generally control the embryo growth process such as by regulating the fluid environment surrounding each embryo within the cartridge.

If fertilized embryos have been placed into the embryo growth tanks 114, the system may flush each embryo growth tank 114 with fluid from one or more of fluid media reservoirs 142a, 142b and 142c. In this manner, cellular debris, waste by-products and other potentially harmful materials may be flushed from each embryo growth tank 114. In addition, fluid flushing will help to ensure that fresh growth media is present within each embryo growth tank 114. By way of example, first fluid media 124 housed within fluid media reservoir 142a may comprise a fluid suitable for flushing each embryo growth tank 114, and second and third fluid media 126 and 128 may comprise embryo growth media. Second fluid media 126 may comprise a fluid media suitable for culturing embryos from the period following fertilization until the embryo comprises between about six and about eight cells (typically two to three days following fertilization), such as P-1 media available from Irvine Scientific. Third fluid media 128, on the other hand, may comprise a different fluid media which is suitable for culturing embryos from the 6–8 cell stage to the blastocyst stage (typically 150–300 cells, about five days after fertilization), such as modified Hams F-10 media (also available from Irvine Scientific).

When fertilization is accomplished within cartridge 112, flushing of each embryo growth tank 114 may be even more advantageous. After the cartridge has been inserted into main system housing 110, cartridge 112 may be allowed to remain undisturbed for a predetermined period of time (such as 6–24 hours) in order to allow fertilization to take place. Fertilization can even be observed using the visualization system described previously, particularly since the visualization system (and in particular the camera and or lens components thereof) may be configured to provide significantly magnified images of the interior of well 130. After fertilization has taken place, each embryo growth tank 114 may be flushed with first fluid 124 from media reservoir 142a. This flushing step will help to remove cellular debris from the embryo, as well as removing sperm and other materials from the embryo growth tank. Thus, porous base 131 of embryo well 130 is preferably configured to allow for the passage of sperm and other cellular debris therethrough, while not allowing passage of the fertilized egg. After the flushing step, the growth process for embryos fertilized within and outside of cartridge 112 may be the same.

It is also contemplated that unfertilized eggs may first be placed into the tanks, and the cartridge then placed into main system housing 110. Thereafter, each tank 114 may be flushed with fluid media in order to remove the cumulus (i.e., cellular debris) from the exterior of the egg and facilitate fertilization. Fluid may even be pulsed into each tank 114 for the purpose of removing cumulus from the surface of the unfertilized egg. Thereafter, the cartridge may be removed, sperm added, and the fertilization process allowed to take place in the manner described above.

After flushing each embryo growth tank 114 containing a fertilized egg with first fluid media 124, second fluid 126 may be urged into each embryo growth tank 114, under the control of CPU 196. CPU 196 will ensure that the fluid temperature within cartridge 112, as well as the fluid flow rate and pressure are suitable for proper embryo growth and development. While second fluid 126 may be continuously flowed into embryo growth tanks 114, thereby providing a constant replacement of fluid growth media, second fluid media 126 may be intermittently urged into each embryo growth tank 114. In this manner, waste by-products will be periodically flushed from each embryo growth tank 114, and fresh fluid media will be provided to each embryo in order to optimize embryo growth. The fluid temperature within cartridge 112 should be maintained between about 97 and about 99° C., and the fluid pressure within cartridge 112 should be between about 0.9 and about 1.2 atmospheres in the first day of embryo growth.

As the embryo grows, the fluid temperature within cartridge 112 may be maintained within the range indicated above. The fluid pressure, however, is preferably increased as a function of embryo growth (as measured, for example, by the cell count or optical density), and/or a function of the time period post-fertilization. For example, once the embryo has grown to 50–100 cells and/or 3–4 days after fertilization, the fluid pressure within cartridge 112 may be increased to between about 1.0 and about 1.3 atmospheres. Thereafter, the fluid pressure may remain constant, or may continue to increase slightly with embryo growth and/or the time period after fertilization, such that the fluid pressure within cartridge 112 will be between about 1.0 and about 1.3 atmospheres when the embryo has reached the blastocyst stage (typically about five days after fertilization). It is believed that increasing the fluid pressure surrounding the embryo in this manner will assist in proper embryo growth, and improve the success rate when implantation of the embryo is attempted.

Once the embryo has grown to between about 6 and about 8 cells, and/or about 2–3 days after fertilization, third fluid media 128 housed within media reservoir 142c may be provided to cartridge 112. The changeover from second fluid media 126 and third fluid 128 may be gradual, such that the fluid surrounding the growing embryo is not abruptly changed from second fluid media 126 to third fluid media 128. It will be recognized that the change to a new form of fluid media can be readily accomplished without manipulating or otherwise disturbing the growing embryo. Similarly, other conditions within each embryo growth tank 114 can be monitored, analyzed and/or altered without disturbing the growing embryo. Typically, the embryo will remain in third fluid media 128 for about two days until it reaches the blastocyst stage. In addition, each embryo within cartridge 112 can be separately monitored in order to determine its growth progress, as well as to provide the optimal fluid environment surrounding the embryo. Once again, third fluid media 128 may be continuously urged into each embryo growth tank 114 or alternatively may be intermittently urged into each embryo growth tank 114. In this manner, waste by-products and other deleterious materials will be removed from the environment surrounding the growing embryo.

Once one or more of the embryos have reached the blastocyst stage, cartridge 112 may be removed from main system housing 110. Thereafter, each blastocyst may be removed from its embryo growth tank 114, such as by use of a syringe inserted through septum 134. Thereafter, the blastocyst may be inserted into the mother for implantation. Since multiple embryos may be grown in cartridge 112, multiple blastocysts may be grown for purposes of implantation. However, since the IVFT device of the present invention may monitor and analyze the growth of each embryo, the IVFT device may be used to determine which blastocysts are the best candidates for a successful pregnancy. For example, the IVFT device may be configured such that the CPU will determine embryo growth (e.g., on the basis of cell count) as a function of time after fertilization. This data may be displayed to the user such that the user may then determine which of the embryos grew optimally (i.e., a growth rate which most closely resembles previously determined optimal growth rates). The IVFT device itself may even determine which of the blastocysts grew at the optimal rate (i.e., not too fast and not too slow), and provide an indication to the user which blastocysts are the best candidates for a successful pregnancy. In this manner, the number of blastocysts inserted into the mother can be reduced, thereby avoiding the implantation of multiple embryos. In fact, it is contemplated that the IVFT device of the present invention will allow for the insertion of a single blastocyst into the mother, with a high probability of a successful pregnancy. This will also allow the number of eggs collected from the mother to be reduced, and, in some instances, may negate the need to provide drugs to stimulate increased egg development prior to egg collection.

In addition, the IVFT device may also determine which embryos are growing optimally prior to the blastocyst stage, such that defective embryos may be discarded at any point after fertilization if it is determined (either by a user of the IVFT device) that an embryo is unlikely to lead to a successful pregnancy. For example, if the IVFT device determines that the optical density of a particular embryo has not increased over during a predetermined period of time (e.g., 24 hours), the device may actuate an alarm indicating which embryo should be discarded (due to improper growth).

It should be pointed out that the above description of the embryo growth process using the IVFT device according to various embodiments of the present invention is merely exemplary. Thus, various types of fluid media may be employed in the IVFT device, including more than three distinct fluid media (such as by providing additional fluid media reservoirs 142 within the IVFT device). In addition, although the above description describes the growth of embryos to the blastocyst stage (which typically occurs about five days after fertilization), the IVFT device of the present invention may also be effectively used to grow embryos to an earlier development stage. For example, the practitioner may use the IVFT device of the present invention to grow the embryos to the 6–8 cell stage (typically about three days after fertilization), and thereafter insert one or more of these embryos into the mother for purposes of implantation. Thus, the IVFT device of the present invention is not limited to growing embryos to the blastocyst stage.

Accordingly, the scope of the present invention should be considered in terms of the following claims, and it is understood not to be limited to the details of the structure and operation shown and described in the specification and the drawings.

What is claimed is:

1. A method for the in vitro development of an embryo in a fluid, comprising the steps of:
   providing an in vitro fallopian tube device comprising a chamber for holding the fluid, said chamber being in fluid communication with said fluid, a circulator for circulating the fluid, and a container for holding the embryo, said container being in fluid communication with said chamber;
   inserting the embryo in the container;
   circulating fluid within the chamber responsive to the growth state of said embryo; and
   exchanging fluid in the chamber responsive to the growth state of said embryo without the need to manipulate the embryo.

2. The method of claim 1, wherein the step of exchanging the media comprises removing fluid from the chamber to a collection reservoir and inserting new fluid into the chamber.

3. The method of claim 1, further comprising the steps of:
   providing a sensor system in the fluid of the chamber;
   monitoring the condition of the fluid of the chamber; and
   displaying the condition of the fluid of the chamber.

4. The method of claim 1, further comprising the steps of:
   developing the embryo until it reaches the blastocyst stage;
   transferring the blastocyst from the device to the uterus of a female.

5. The method of claim 1, further comprising the steps of:
   providing a control system with alarm levels for the condition of the fluid; and
   comparing the condition of the fluid with the alarm levels.

6. The method of claim 5, further comprising the step of exchanging fluid of the chamber if the condition of the fluid is outside the alarm level.

7. A method for the in vitro development of an embryo in a fluid comprising the steps of:
   providing an in vitro fallopian tube device comprising a chamber for holding the fluid, and a container for holding the embryo;
   inserting the embryo in the container; and
   exchanging fluid in the chamber without manipulating the embryo.

8. A method for the in vitro development of an embryo, comprising:
   (a) providing a tank having an embryo and a first fluid therein;
   (b) monitoring the growth of said embryo; and
   (c) adjusting conditions within said tank in response to the results of said monitoring step.

9. The method of claim 8, wherein said step of monitoring the growth of said embryo comprises monitoring the nuclear mass of the embryo.

10. The method of claim 8, wherein said step of monitoring the growth of said embryo comprises counting the number of cells in said embryo.

11. The method of claim 8, wherein said step of monitoring the growth of said embryo comprises measuring the optical density of the embryo.

12. The method of claim 11, wherein said step of measuring the optical density of the embryo comprises directing light at said embryo, and measuring the amount of light transmitted through said embryo.

13. The method of claim 8, wherein said step of adjusting conditions within said tank comprises at least one of: adjusting the fluid pressure within said tank, flowing fluid into said tank and adjusting the temperature within said tank.

14. The method of claim 8, wherein said step of adjusting conditions within said tank comprises increasing the fluid pressure within said tank as the nuclear mass of said embryo increases.

15. The method of claim 8, wherein said tank includes a fluid outlet, and wherein said step of adjusting conditions within tank comprises adding new fluid to said tank while allowing said first fluid already in said tank to be removed from the tank through said fluid outlet.

16. The method of claim 8, wherein said step of monitoring the growth of said embryo comprises monitoring the nuclear mass of the embryo, and wherein said step of adjusting conditions within said tank comprises replacing said first fluid with a second fluid after the nuclear mass of the embryo has reached a predetermined level, wherein said replacing step is accomplished without manipulating said embryo.

17. The method of claim 8, wherein a plurality of tanks, each having an embryo and a first fluid therein, are provided.

18. The method of claim 17, wherein said step of monitoring the growth of said embryos comprises monitoring the rate of growth of said embryos over a period of time, and further comprising the step of selecting one or more of said embryos for insertion into a recipient based upon the rate of growth of said embryos.

19. A method for the in vitro development of an embryo, comprising:
   (a) providing a tank having an embryo therein, said tank in fluid communication with at least first and second sources of fluid;
   (b) flowing fluid from at least said first fluid source into said tank; and
   (c) thereafter, flowing fluid from at least said second fluid source into said tank.

20. The method of claim 19, wherein said tank has a fluid inlet and a fluid outlet, and wherein fluid is urged out of the tank through said fluid outlet as fluid is flowed into the tank through said fluid inlet.

21. The method of claim 19, wherein fluid is continuously flowed into said tank.

22. The method of claim 19, wherein fluid is periodically flowed into said tank.

23. The method of claim 22, wherein fluid is periodically flowed into said tank in response to at least one of: a predetermined schedule, the nuclear mass of the embryo, a sensed condition within said tank, and a sensed condition of fluid urged out of said tank.

24. The method of claim 20, wherein the step of flowing fluid from at least said second fluid source into said tank commences in response to at least one of: a predetermined schedule, the nuclear mass of the embryo, a sensed condition within said tank, and a sensed condition of fluid urged out of said tank.

25. The method of claim 19, wherein fluid is flowed into said tank by a pump.

26. The method of claim 19, wherein said first and second sources of fluid are pressurized such that fluid is flowed into said tank by the pressure within said fluid sources.

* * * * *